(12) United States Patent
Otsuka et al.

(10) Patent No.: US 11,521,575 B2
(45) Date of Patent: Dec. 6, 2022

(54) ELECTRONIC DEVICE, ELECTRONIC DEVICE CONTROL METHOD, AND MEDIUM

(71) Applicant: CASIO COMPUTER CO., LTD., Tokyo (JP)

(72) Inventors: Toshihiko Otsuka, Ome (JP); Takahiro Tomida, Hamura (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 2 days.

(21) Appl. No.: 17/080,910

(22) Filed: Oct. 27, 2020

(65) Prior Publication Data

US 2021/0134243 A1 May 6, 2021

(30) Foreign Application Priority Data

Oct. 30, 2019 (JP) .............................. JP2019-197860

(51) Int. Cl.
*G09G 5/02* (2006.01)
*A61B 5/021* (2006.01)
*A61B 5/00* (2006.01)
*G09G 5/10* (2006.01)
*A61B 5/026* (2006.01)

(52) U.S. Cl.
CPC ............. *G09G 5/02* (2013.01); *A61B 5/0261* (2013.01); *A61B 5/02108* (2013.01); *A61B 5/742* (2013.01); *G09G 5/10* (2013.01); *G09G 2320/0626* (2013.01); *G09G 2354/00* (2013.01); *G09G 2380/08* (2013.01)

(58) Field of Classification Search
CPC ............. G09G 5/02; G09G 2320/0626; G09G 2354/00; G09G 2380/08; A61B 5/02108; A61B 5/0261; A61B 5/742; A61B 5/021
See application file for complete search history.

(56) References Cited

U.S. PATENT DOCUMENTS

2018/0042486 A1  2/2018 Yoshizawa et al.

FOREIGN PATENT DOCUMENTS

JP          2016190022 A    11/2016

*Primary Examiner* — Antonio A Caschera
(74) *Attorney, Agent, or Firm* — Holtz, Holtz & Volek PC

(57) ABSTRACT

An electronic device includes an information acquisition unit, a display information determination unit, and a display control unit. The information acquisition unit acquires first pulse wave information indicating a pulse wave of a part of a body based on image information of the body in a first image obtained by imaging at least the part of the body, and acquires second pulse wave information indicating a pulse wave of a part of the body based on image information of the body in a second image obtained by imaging the part of the body after the first image has been obtained. The display information determination unit determines a display range of a display color of a display image or brightness corresponding to a blood flow variation of a part of the body based on first pulse wave information and second pulse wave information. The display control unit controls display of the display image by the display color determined based on the display range or brightness and the second pulse wave information.

19 Claims, 18 Drawing Sheets

SELF-STANDING OBTAINED BY
ROTATING LEG PORTION WITH
HINGE PORTION AS CENTER

DISPLAY EXAMPLE OF
FIRST DISPLAY RANGE

DISPLAY EXAMPLE OF
THIRD DISPLAY RANGE

MAXIMUM VALUE: 6
MINIMUM VALUE: 3

MAXIMUM VALUE: 9
MINIMUM VALUE: 0

DISPLAY EXAMPLE OF FIRST DISPLAY RANGE

DISPLAY EXAMPLE OF THIRD DISPLAY RANGE

MAXIMUM VALUE: 5
MINIMUM VALUE: 0

MAXIMUM VALUE: 9
MINIMUM VALUE: 4

DISPLAY EXAMPLE OF FIRST DISPLAY RANGE

DISPLAY EXAMPLE OF THIRD DISPLAY RANGE

MAXIMUM VALUE: 9
MINIMUM VALUE: 0

MAXIMUM VALUE: 9
MINIMUM VALUE: 0

ELECTRONIC DEVICE, ELECTRONIC DEVICE CONTROL METHOD, AND MEDIUM

CROSS-REFERENCE TO RELATED APPLICATIONS

This application is based upon and claims the benefit of priority under 35 USC 119 of Japanese Patent Application No. 2019-197860 filed on Oct. 30, 2019, the entire disclosure of which, including the description, claims, drawings, and abstract, is incorporated herein by reference in its entirety.

BACKGROUND OF THE INVENTION

1. Field of the Invention

The present invention relates to an electronic device, an electronic device control method, and a medium.

2. Description of the Related Art

JP 2016-190022 A discloses a configuration in which blood flow variations before and after bathing are compared and the blood flow variations of a body after bathing is displayed by hatching in order to provide notification of any part of the body where the bathing is effective for the blood flow variation.

BRIEF SUMMARY OF THE INVENTION

An electronic device includes at least one processor, wherein the processor performs:
acquiring first pulse wave information indicating a pulse wave of a part of a body based on image information of the body in a first image obtained by imaging at least the part of the body;
acquiring second pulse wave information indicating a pulse wave of the part of the body based on image information of the body in a second image obtained by imaging the part of the body after the first image has been obtained;
determining a display range of a display color of a display image corresponding to the blood flow variation of the part of the body based on the first pulse wave information and the second pulse wave information; and
controlling display of the display image by the display color determined based on the display range and the second pulse wave information.

An electronic device includes at least one processor, wherein the processor performs:
acquiring first pulse wave information indicating a pulse wave of a part of a body based on image information of the body in a first image obtained by imaging at least the part of the body;
acquiring second pulse wave information indicating a pulse wave of the part of the body based on image information of the body in a second image obtained by imaging the part of the body after the first image has been obtained;
determining brightness of display of a display image corresponding to the blood flow variation of the part of the body based on the first pulse wave information and the second pulse wave information; and
controlling display of the display image by a display color determined based on the brightness of the display and the second pulse wave information.

A control method of an electronic device, which measures a blood flow based on an image of a body and includes at least one processor, is performed by the processor and includes:
acquiring first pulse wave information indicating a pulse wave of a part of the body based on image information of the body in a first image obtained by imaging at least the part of the body;
acquiring second pulse wave information indicating a pulse wave of the part of the body based on image information of the body in a second image obtained by imaging the part of the body after the first image has been obtained;
determining a display range of a display color of a display image corresponding to the blood flow variation of the part of the body based on the first pulse wave information and the second pulse wave information; and
controlling display of the display image by the display color determined based on the display range and the second pulse wave information.

A non-transitory computer-readable recording medium includes a control program of an electronic device, which measures a blood flow based on an image of a body, stored thereon, the control program, when executed on at least one processor in a computer of the electronic device, causing the computer to perform:
acquiring first pulse wave information indicating a pulse wave of a part of a body based on image information of the body in a first image obtained by imaging at least the part of the body;
acquiring second pulse wave information indicating a pulse wave of the part of the body based on image information of the body in a second image obtained by imaging the part of the body after the first image has been obtained;
determining a display range of a display color of a display image corresponding to the blood flow variation of the part of the body based on the first pulse wave information and the second pulse wave information; and
controlling display of the display image by the display color determined based on the display range and the second pulse wave information.

A control method of an electronic device, which measures a blood flow based on an image of a body and includes at least one processor, is performed by the processor and includes:
acquiring first pulse wave information indicating a pulse wave of a part of the body based on image information of the body in a first image obtained by imaging at least the part of the body;
acquiring second pulse wave information indicating a pulse wave of the part of the body based on image information of the body in a second image obtained by imaging the part of the body after the first image has been obtained;
determining brightness of display of a display image corresponding to the blood flow variation of the part of the body based on the first pulse wave information and the second pulse wave information; and
controlling display of the display image by a display color determined based on the brightness of the display and the second pulse wave information.

A non-transitory computer-readable recording medium includes a control program of an electronic device, which measures a blood flow based on an image of a body, stored thereon, the control program, when executed on at least one processor in a computer of the electronic device, causing the computer to perform:

acquiring first pulse wave information indicating a pulse wave of a part of a body based on image information of the body in a first image obtained by imaging at least the part of the body;

acquiring second pulse wave information indicating a pulse wave of the part of the body based on image information of the body in a second image obtained by imaging the part of the body after the first image has been obtained;

determining brightness of display of a display image corresponding to the blood flow variation of the part of the body based on the first pulse wave information and the second pulse wave information; and controlling display of the display image by a display color determined based on the brightness of the display and the second pulse wave information.

DETAILED DESCRIPTION OF THE INVENTION

Hereinafter, an embodiment of the invention will be described with reference to the drawings.

[Outline of Embodiment]

An electronic device 1 according to an embodiment of the invention is a smart mirror configured as a self-standing mirror that can be carried by a user. The electronic device 1 images a user as a target person who visually recognizes the mirror. The electronic device 1 acquires a blood flow variation before and after a specific action such as massage based on an image of the user, and displays a hue moving image according to the degree of blood flow variation. According to such an electronic device 1, it is possible to display the blood flow variation before and after the specific action in an easily understandable manner

[System Configuration]

Figure 1:
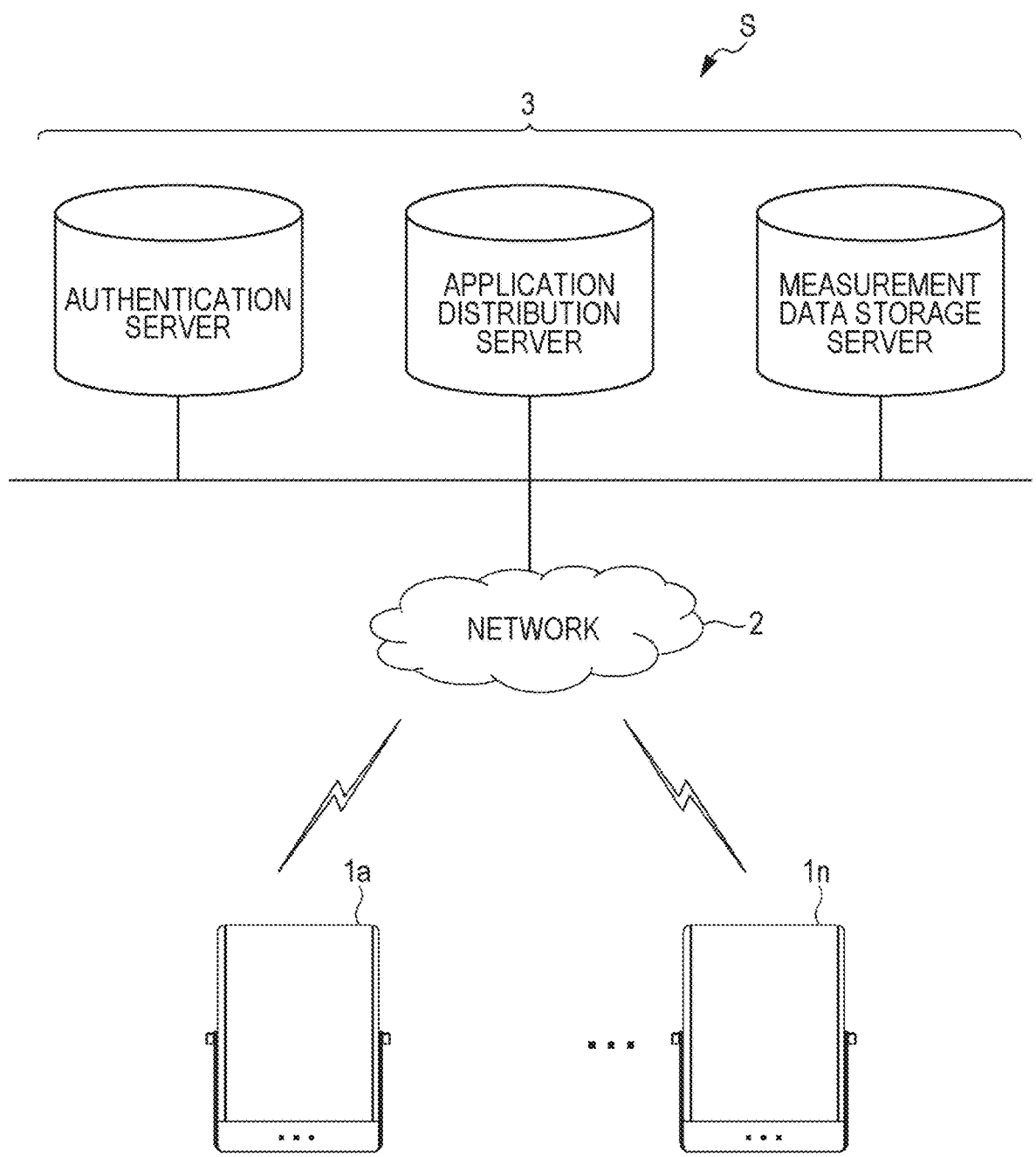
FIG. 1 is a configuration diagram illustrating a configuration of a measurement system according to an embodiment of the invention.

FIG. 1 is a block diagram illustrating an overall configuration of a measurement system S including the electronic device 1 according to the embodiment. As illustrated in FIG. 1, the measurement system S includes a plurality of the electronic devices 1, a network 2, and a server group 3. The number of electronic devices 1 is not particularly limited, and the measurement system S may include n (n is an arbitrary natural number) electronic devices 1. In the following description, an alphabet at the end of the reference sign is omitted and simply referred to as "electronic device 1" when the n electronic devices 1 are described without distinction.

The electronic device 1 is a measurement device that measures the blood flow variation of a user from the image and displays a measurement result. The electronic device 1 is connected to each of servers included in the server group 3 via the network 2 so as to be capable of communicating with each other.

The network 2 is implemented by, for example, the Internet, a local area network (LAN), a mobile phone network, or a network combining these.

The server group 3 includes various servers that cooperate with the electronic device 1. For example, the server group 3 includes an authentication server configured to authenticate the user of the electronic device 1. For example, the server group 3 further includes an application distribution server that distributes application software to implement a function of the electronic device 1. For example, the server group 3 further includes a measurement data storage server that stores user profile information which is information including setting information on the user, use history of the electronic device 1 by the user, and the like.

Note that the measurement system S illustrated in FIG. 1 is merely an example, and the server group 3 may include servers having other functions. Further, the plurality of servers included in the server group 3 may be implemented by separate server devices, or may be implemented by a single server device.

[Exterior Structure]

Figure 2:
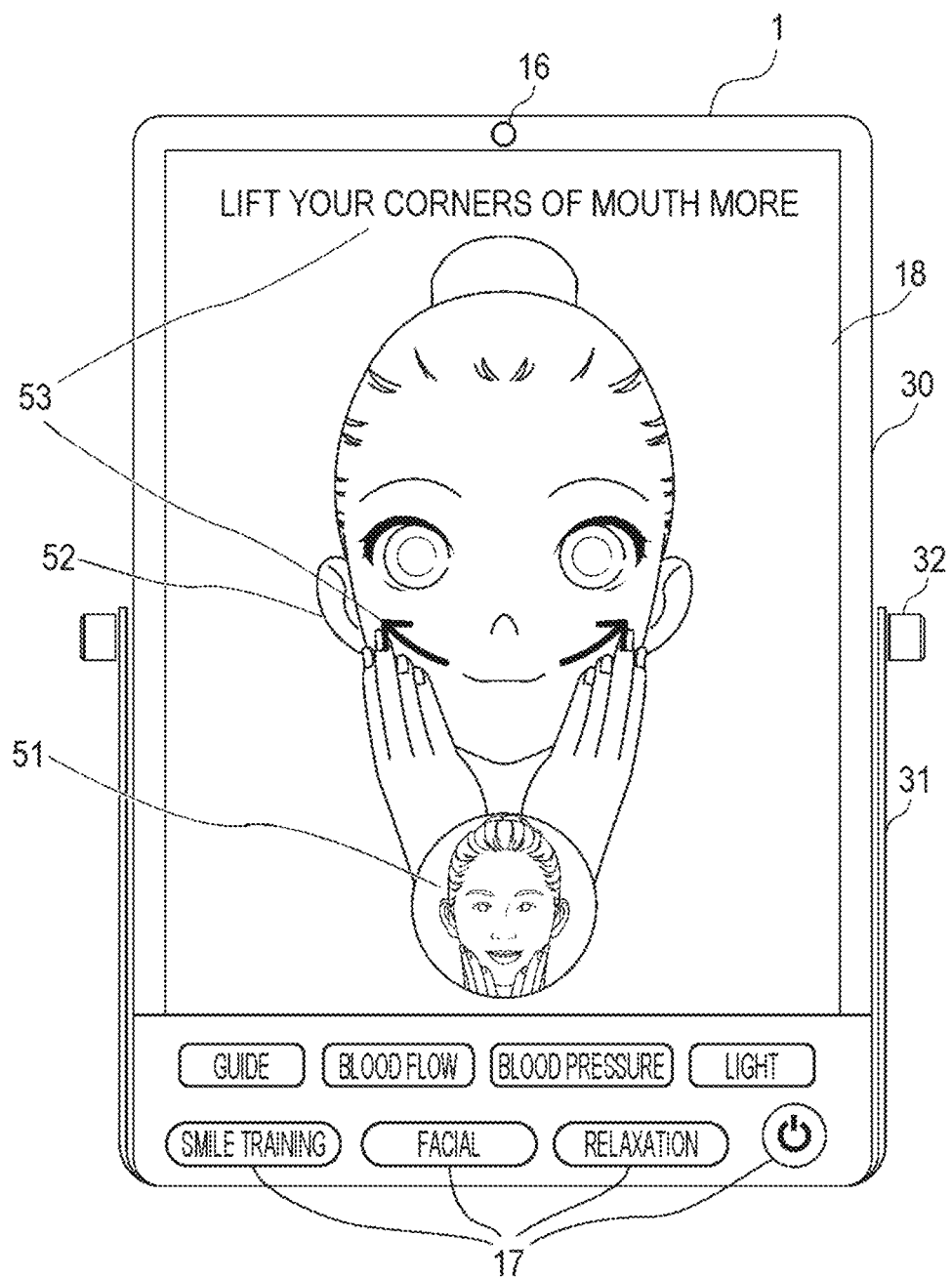
FIG. 2 is a configuration view illustrating an exterior structure of a front surface of an electronic device according to an embodiment of the invention.
Figure 3A:
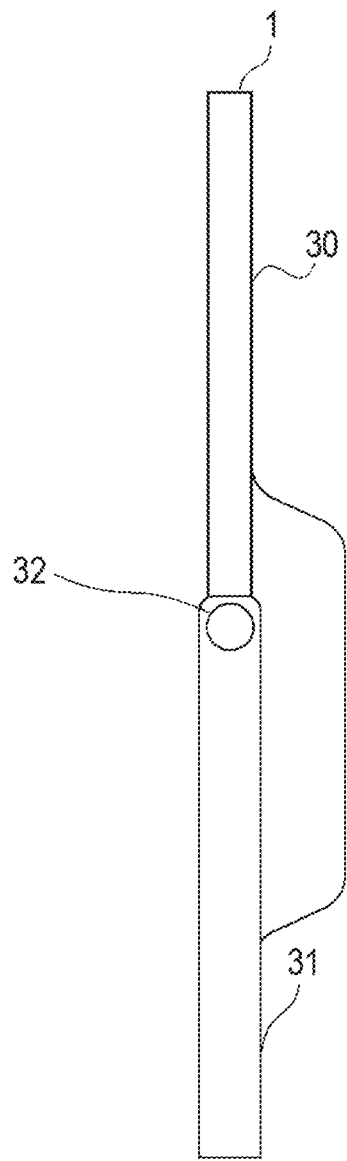
FIGS. 3A and 3B are configuration views illustrating an exterior structure of a side surface of the electronic device according to the embodiment of the invention.
Figure 3B:
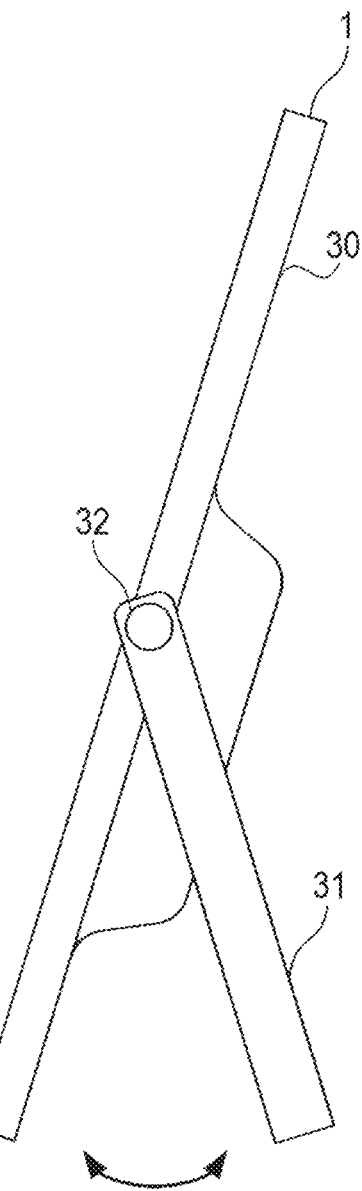

FIG. 2 is a configuration diagram illustrating an exterior structure of a front surface of the electronic device 1 according to the embodiment of the invention. FIGS. 3A and 3B are configuration views illustrating an exterior structure of a side surface of the electronic device 1. A size of the front surface of the electronic device 1 is formed to, for example, an A4 size defined by international organization for standardization (ISO) 216 which is an international standard.

As illustrated in FIGS. 2 to 3B, the electronic device 1 includes a body portion 30, a leg portion 31, and a hinge portion 32. The body portion 30 is a part including a display unit 18 and other hardware to be described later with reference to FIG. 4. Further, the leg portion 31 and the hinge portion 32 are members configured to make the electronic device 1 stand alone. The leg portion 31 is rotatably supported by the hinge portion 32 with respect to the body portion 30.

As illustrated in FIG. 3A, when carrying the electronic device 1, a user can carry the electronic device 1 in a non-bulky shape by aligning a side surface of the body portion 30 and a side surface of the leg portion 31. On the other hand, as illustrated in FIG. 3B, when the electronic device 1 is installed on a desk or the like and used, the user rotates the leg portion 31 with the hinge portion 32 as the center point so that the electronic device 1 can be installed to stand alone. Note that the hinge portion 32 has a mechanism for holding the leg portion 31 in the state of maintaining a predetermined angle in order to enable self-standing of the electronic device 1.

The body portion 30 includes the display unit 18 as described above. The display unit 18 is a part that displays various kinds of information to display the various kinds of information to the user. The display unit 18 displays, for example, a user image (corresponding to a user image 51 in the drawing), which is a subject of an actual image of the user imaged by the imaging unit 16, an avatar image (corresponding to an avatar image 52 in the drawing), which is a substitute image for the user, and a guide image (corresponding to a guide image 53 in the drawing) which is auxiliary information to provide guidance. In this case, the guide image is combined with the avatar image and displayed in a superimposed manner on the display unit 18.

The user can grasp the various kinds of information at once by visually recognizing the display unit 18. Note that such display on the display unit 18 has no visible gap and has a sense of unity suitable for the user to visually recognize as described above.

As illustrated in FIG. 2, the electronic device 1 further includes the imaging unit 16, an input unit 17, and the display unit 18 as the exterior structure.

The imaging unit 16 is a unit that images the user facing the display unit 18 as a subject at the time of using the electronic device 1. The imaging unit 16 is arranged at a position where a face image of the user facing the display unit 18 can be imaged. For example, the imaging unit 16 is arranged on a front surface of the body portion 30 above the display unit 18 as illustrated in the drawing.

The input unit 17 is a unit that receives an operation input by the user. The input unit 17 is implemented by a plurality of buttons, for example. The drawing illustrates, as an example, a button for switching to various modes such as small face beauty treatment, smile training, and recording of biometric information, and a button for switching between on and off of the power of the electronic device 1.

The exterior structure of the electronic device 1 has been described as above. However, this structure is merely an example, and the exterior structure of the electronic device 1 is not limited to this example.

For example, the electronic device 1 may further include a light emitting unit that emits light in order to illuminate the user facing the display unit 18. The electronic device 1 functions as a mirror with an illumination when the light emitting unit adjusts illuminance and a color component to illuminate the user. The number of the light emitting units may be plural. The light emitting unit may be arranged above or below the display unit 18, or may be arranged in the entire periphery of the display unit 18.

For example, the number and arrangement of the input units 17 may be changed. For example, a part of the display unit 18 may be configured as a touch panel, and the input unit 17 and the display unit 18 may be integrally configured.

[Hardware Configuration]

Figure 4:
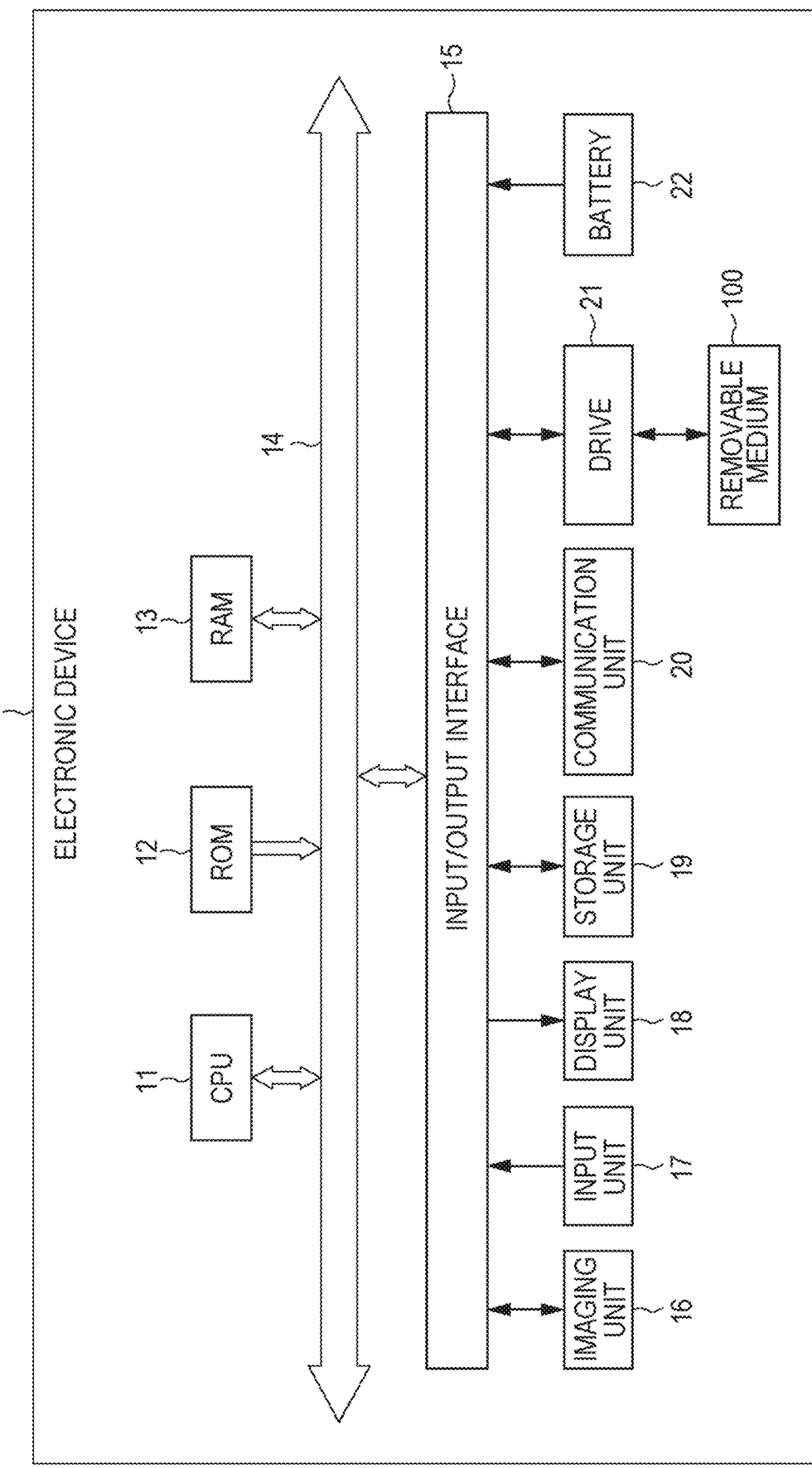
FIG. 4 is a block diagram illustrating a configuration of hardware of the electronic device according to the embodiment of the invention.

FIG. 4 is a block diagram illustrating a hardware configuration of the electronic device 1.

As illustrated in FIG. 4, the electronic device 1 includes a central processing unit (CPU) 11 (processor) which is a processor, a read only memory (ROM) 12, a random access memory (RAM) 13, a bus 14, an input/output interface 15, the imaging unit 16, the input unit 17, the display unit 18, a storage unit 19, a communication unit 20, a drive 21, and a battery 22.

The CPU 11 executes various processes according to a program recorded in the ROM 12 or a program loaded from the storage unit 19 onto the RAM 13.

The RAM 13 also appropriately stores data and the like necessary for the CPU 11 to execute the various processes.

The CPU 11, the ROM 12, and the RAM 13 are connected to each other via the bus 14.

The input/output interface 15 is also connected to the bus 14. The imaging unit 16, the input unit 17, the display unit 18, the storage unit 19, the communication unit 20, the drive 21, and the battery 22 are connected to the input/output interface 15.

Although not illustrated, the imaging unit 16 includes an optical lens unit and an image sensor. The optical lens unit includes lenses that collect light, such as a focus lens and a zoom lens, to image a subject. The focus lens is a lens that forms a subject image on a light receiving surface of the image sensor. The zoom lens is a lens that freely changes a focal length within a certain range. The imaging unit 16 is also provided with a peripheral circuit that adjusts setting parameters, such as focus, exposure, and white balance, if necessary.

The image sensor includes a photoelectric conversion element, an analog front end (AFE), and the like. The photoelectric conversion element includes, for example, a complementary metal oxide semiconductor (CMOS) type photoelectric conversion element. The subject image is incident onto the photoelectric conversion element from the optical lens unit. Therefore, the photoelectric conversion element photoelectrically converts (images) the subject image, accumulates image signals for a predetermined time, and sequentially supplies the accumulated image signals to the AFE as analog signals. The AFE executes various kinds of signal processing, such as A/D (Analog/Digital) conversion processing, on the analog image signal. A digital signal is generated by the various kinds of signal processing and is output as an output signal of the imaging unit 16. Such an output signal of the imaging unit 16 is appropriately supplied to the CPU 11 and the like.

The input unit 17 includes various buttons, a microphone, and the like, and inputs various kinds of information according to a user's instruction operation or instruction voice.

The display unit 18 includes a liquid crystal display or the like, and displays an image corresponding to image data output by the CPU 11.

The storage unit 19 includes a semiconductor memory such as a dynamic random access memory (DRAM) and stores various kinds of data.

The communication unit 20 performs communication control for the CPU 11 to communicate with other devices (for example, the respective servers included in the server group 3) via the network 2.

The drive 21 includes an interface to which a removable medium 100 can be attached. The removable medium 100 including a magnetic disk, an optical disk, a magneto-optical disk, a semiconductor memory, or the like is appropriately attached to the drive 21. The removable medium 100 stores a program configured to execute a combination display process to be described later, and various kinds of data such as image data. The program read from the removable medium 100 by the drive 21 and various kinds of data such as image data are installed in the storage unit 19 if necessary.

The battery 22 is configured to supply power to the respective units and to be rechargeable by being connected to an external power source. When the electronic device 1 is not connected to the external power supply, the electronic device 1 is operated by the power of the battery 22.

The electronic device 1 may further include other hardware in addition to the above hardware. For example, the electronic device 1 may include a lamp, a speaker, a vibration motor, and the like, and may further include an output unit that outputs light, voice, or a vibration signal.

[Functional Configuration]

Figure 5:
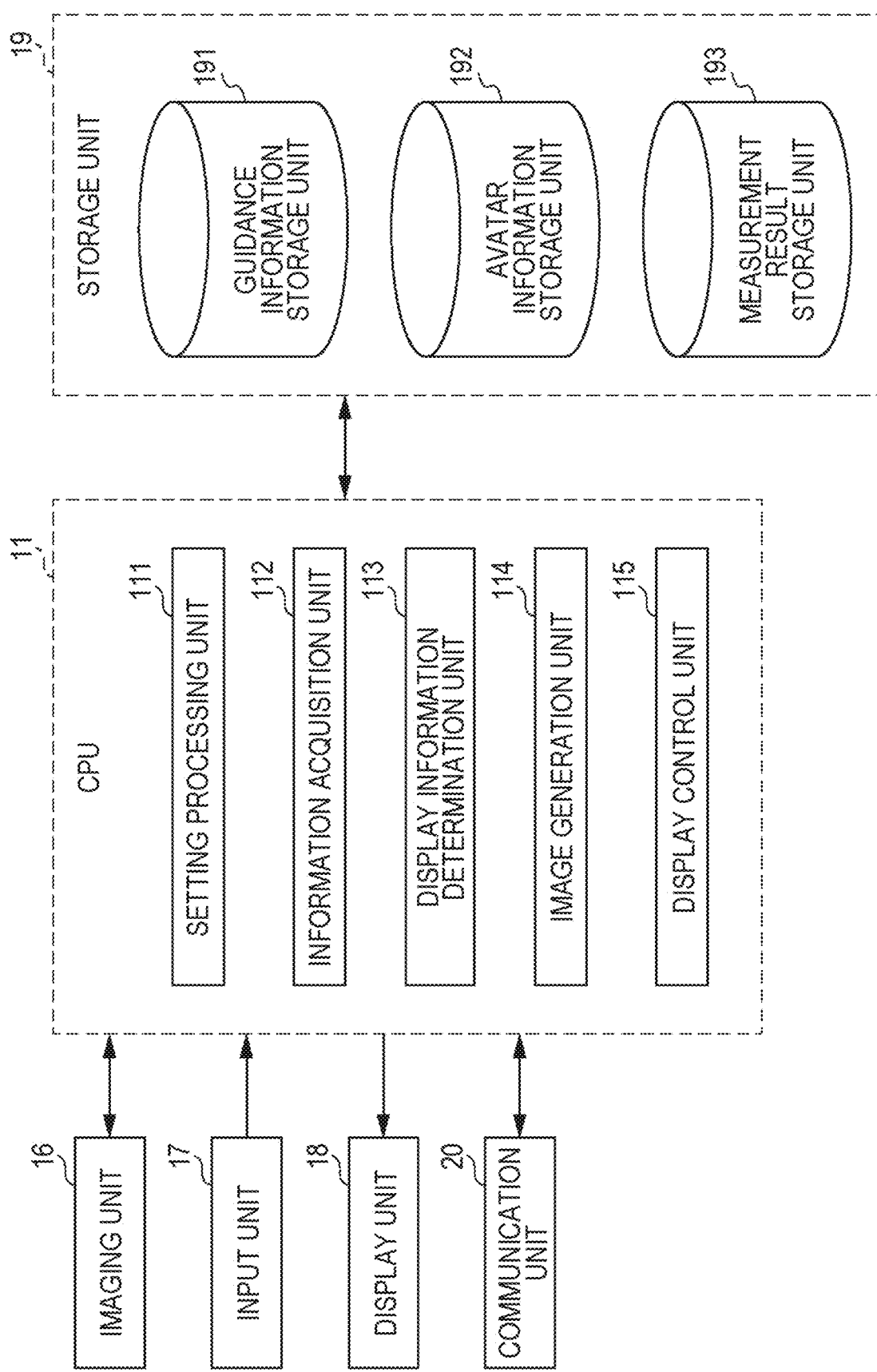
FIG. 5 is a functional block diagram illustrating a functional configuration for execution of a measurement process among functional configurations of the electronic device according to the embodiment of the invention.

FIG. 5 is a functional block diagram illustrating a functional configuration for execution of a measurement process among functional configurations of the electronic device 1. The measurement process is a series of processes in which the electronic device 1 displays a measurement result based on a change of a biometric information value acquired from a user.

First, the storage unit 19 that stores various kinds of information will be described. As illustrated in FIG. 5, a guidance information storage unit 191, an avatar information storage unit 192, and a measurement result storage unit 193 are set in one area of the storage unit 19.

The guidance information storage unit 191 stores various kinds of data regarding guidance in a display process For example, the guidance information storage unit 191 stores data of a guide image, text data, sound data, and the like for generation of guidance information to be displayed in the display process. In addition, the guidance information storage unit 191 also stores a display order of a plurality of pieces of guidance information in a series of guidance, a condition for switching from guidance information to be displayed to the next guidance information, data for generation of various user interfaces, and the like. The guidance information storage unit 191 further stores profile information of the user generated regarding the display process. The guide image may be image data generated in advance or may be computer graphics (CG) or the like generated in real time based on calculation.

The avatar information storage unit 192 stores various kinds of data regarding the avatar which is the substitute for the actual image of the user. For example, the avatar information storage unit 192 stores data of avatar images, a condition for display of which avatar image in guidance, and the like for generation of the avatar image to be displayed in the combination display process. The avatar image may be image data generated in advance, or may be CG or the like generated in real time based on calculation. The avatar image is, for example, an image of a character imitating a human or an animal. Further, any number of avatar images may be prepared, and the avatar image may be appropriately selected according to an attribute of the user (for example, a gender, an age, and a preference of the user) and a content of guidance. Further, the avatar image may be a continuous image group for implementation of animation display of a character or the like. Further, each data may be stored as one library in each guidance unit so as to be easily read at the time of implementing a series of guidance.

The measurement result storage unit 193 stores information for the information acquisition unit 112 to perform measurement, information for display of a measurement result, information indicating the measurement result, and the like. The measurement process performed by the information acquisition unit 112 will be described later.

Note that each information stored in the guidance information storage unit 191, the avatar information storage unit 192, and the measurement result storage unit 193 described above may be stored only in the storage unit 19, but may be appropriately stored in the removable medium 100 by the drive 21. Further, each information stored in the guidance information storage unit 191, the avatar information storage unit 192, and the measurement result storage unit 193 may be appropriately stored in the measurement data storage server or the like included in the server group 3.

Next, each functional block that executes the measurement process will be described. As illustrated in FIG. 5, a setting processing unit 111, an information acquisition unit 112, a display information determination unit 113, an image generation unit 114, and a display control unit 115 function in the CPU 11.

The setting processing unit 111 is a part that controls settings related to the measurement process and display process. The setting processing unit 111 acquires application software for the display process, for example, from the application distribution server included in the server group 3, and runs this application software. The setting processing unit 111 authenticates the user who performs the display process, for example, by communicating with the authentication server included in the server group 3. Further, the setting processing unit 111 updates the profile information of the user in the display process, for example, by communicating with the measurement data storage server included in the server group 3.

The setting processing unit 111 displays a menu to perform guidance based on the application software for the display process. For example, a menu, which includes options to select a content of the guidance, such as "small face beauty treatment", "smile massage", "measurement of biometric information", and "makeup", is displayed based on the guidance. Further, the setting processing unit 111 receives selection of any guidance content from the user referring to the menu via the input unit 17 or the like. For example, the selection of "small face beauty treatment" is received. As a result, the display process is performed for the guidance related to the small face beauty treatment. Note that the small face beauty treatment refers to, for example, a lymphatic massage or the like performed by the user on the user's own face or the like to reduce swelling of the face by the massage that drains lymph.

The information acquisition unit 112 analyzes an image including the user as the subject imaged by the imaging unit 16 to acquire information on the user (hereinafter, referred to as "subject information"). The subject information includes, for example, a coordinate indicating a position of each part on the user's face, a color of each part on the user's face, and biometric information (sometimes called vital data) indicating a user's state.

Coordinate information is set as a premise to perform the measurement process. The coordinate information includes, for example, information to define each coordinate system, such as an imaging coordinate system which is a coordinate system for an image captured by the imaging unit 16 and a display unit coordinate system which is a coordinate system for a display plane of the display unit 18, and information indicating a correspondence to convert a coordinate in each coordinate system to a coordinate in the other coordinate system. Each functional block can perform the display process by converting a coordinate in each coordinate system based on a correspondence of the coordinate between the respective coordinate systems. The correspondence between the respective coordinate systems is set by performing calibration with correction of a correspondence by adjusting a direction of an imaging lens in the imaging unit 16 and adjusting a zoom factor, for example, at the time of manufacturing the electronic device 1. For example, the zoom factor is adjusted using both or any of so-called optical zoom which is performed by adjusting a lens position of the imaging unit 16, and so-called digital zoom in the image processing.

The information acquisition unit 112 performs processing related to face tracking such as pattern matching of a contour and a part and skin color identification on an image obtained by imaging the user to identify a contour of the face, positions of eyes, and a region of the skin, and detects a region of a predetermined part such as the forehead, the cheeks, the chin, and the neck. For example, the contour of the user's face and the positions of the eyes in the image are detected, and, based on relative positions with respect thereto, a plurality of regions such as the forehead, the eyelids, the cheeks, the periphery of the nose, the periphery of the lips, the chin, the neck, and the décolleté, are automatically recognized. Then, the information acquisition unit 112 detects states such as a coordinate of each of the detected regions of parts, a color of the user's skin, and an angle of the user's face (that is, a direction of the user's face).

The information acquisition unit 112 acquires biometric information on a blood flow such as a pulse and a pulse wave based on a green signal absorbed by hemoglobin in the blood under the skin of the user in the image. It is generally said that a wavelength of the green signal is 495 to 570 nm, and hemoglobin has a high absorption coefficient around 550 to 660 nm. Since such a characteristic of the wavelength and a luminance value of the green signal of the image acquired by the imaging unit 16 are used, a change in absorption of hemoglobin can be accurately captured as a change in blood flow rate. When an imaging element of the imaging unit 16 converts light into a luminance, RGB filters are arranged in front of the imaging element, and a luminance value of each pixel of RGB is calculated. In this case, light passing through a green filter becomes the luminance value. Even if the sensitivity of the imaging element is flat with respect to the wavelength, the wavelength band can be narrowed down to some extent by the above-described filters so that the green signal can be detected accurately.

Since the measurement is performed based on the information (image) acquired by the imaging unit 16, the biometric information can be sequentially acquired without touching the user. More specifically, the information acquisition unit 112 sets a region of interest (ROI) based on a part on the user's face or the like. The information acquisition unit 112 acquires the luminance of the green signal at a plurality of locations within the region of interest. The information acquisition unit 112 acquires the luminance of the green signal every unit time and acquires a temporal change in the luminance of the green signal as pulse wave information. Note that the unit time is, for example, a frame rate of a moving image, and the luminance of the green signal can be acquired for each of temporally consecutive images forming the image.

In the embodiment, the user before a specific action is imaged to acquire the first image, and the user after the specific action is imaged to acquire the second image in order to compare states of the blood flow before and after the specific action of the user. Then, the information acquisition unit 112 acquires a temporal change in the luminance of the green signal for each of the first image and the second image. More specifically, the information acquisition unit 112 acquires a luminance value of the green signal analyzed from the image information of the first image as first luminance information and acquires information, which indicates a temporal change of the first luminance information and includes a difference between a peak and a bottom of luminances corresponding to a pulse wave of a part of the body at the time of capturing the first image, as first pulse wave information. Similarly, the information acquisition unit 112 acquires a luminance value of the green signal analyzed from the image information of the second image as second luminance information and acquires information, which indicates a temporal change of the second luminance information and includes a difference between a peak and a bottom of luminances corresponding to a pulse wave of a part of the body at the time of capturing the second image, as second pulse wave information.

The information acquisition unit 112 divides the region of interest into a plurality of small regions to generate a mosaic-shaped hue moving image (see FIGS. 6A and 6B) that visually displays the state of the blood flow of the user and acquires the temporal change of the luminance per small region. For example, when the face is set as the region of interest, the facial part is divided into 30×30 mosaic-shaped small regions. Then, the temporal change in the luminance of the green signal is calculated per small region. The small region includes at least one pixel. When the small region includes a plurality of pixels, an average value of luminances of the plurality of pixels may be acquired as the luminance of the small region. In the embodiment, the information acquisition unit 112 acquires the temporal change in the luminance of the green signal per small region for each of the first image and the second image.

Further, the information acquisition unit 112 acquires pulse wave information to determine a display range, which will be described later, in addition to the information indicating the temporal change in the luminance of the green signal per small region. More specifically, the information acquisition unit 112 acquires information indicating a temporal change of a representative value of the overall luminance of the region of interest of the first image and information indicating a temporal change of a representative value of the overall luminance of the region of interest of the second image. The representative value reflects luminances of green signals at a plurality of locations in the region of interest, and is calculated by various methods such as a mode, a median, and an average value. In the embodiment, a temporal change of an average value of luminances of green signals of all pixels in the region of interest is acquired by the information acquisition unit 112 as the pulse wave information. That is, the first pulse wave information includes at least two kinds of information of information indicating the temporal change of the luminance per small region at the time of imaging the first image and information indicating the temporal change of the average value of luminances of the entire region of interest. Similarly, the second pulse wave information includes at least two kinds of information of information indicating the temporal change of the luminance per small region at the time of imaging the second image and information indicating the temporal change of the average value of luminances of the entire region of interest. Note that a comparison process of comparing the first pulse wave information and the second pulse wave information and a process of generating a hue moving image based on the comparison process will be described later.

As a method for acquiring biometric information from the luminance of the green signal of the image, it is possible to use a technique for acquiring biometric information on a blood flow such as a pulse and a pulse wave based on the green signal absorbed by hemoglobin in the blood under the skin described in the following reference, for example.

REFERENCE

Tohoku University Cyber Science Center Advanced Information Technology Research Department, Tohoku University Innovative Innovation Research Organization, "Success in Development of Blood State Monitoring Device "Magic Mirror"", [online], Sep. 27, 2016, [searched on Sep. 27, 2018], Internet <URL: http://www.tohoku.ac.jp/japanese/newimg/pressimg/tohokuuniv-press20160927_01web.pdf>

Figure 6A:
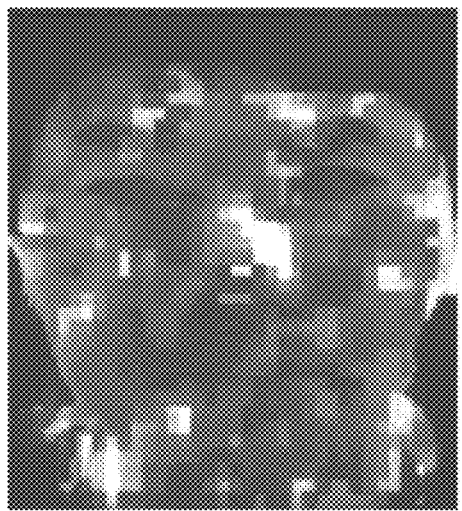
FIGS. 6A and 6B are views illustrating examples of a hue moving image generated by the electronic device according to the embodiment of the invention.
Figure 6B:

The display information determination unit 113 performs a process for generating a hue moving image that displays the measurement result of the information acquisition unit 112. FIG. 6A is an example of a hue moving image illustrating a blood flow of the user's face before a massage treatment (specific action), and FIG. 6B is an example of a hue moving image illustrating a blood flow of the user's face after the massage treatment (specific action). FIGS. 6A and 6B illustrate states where the facial part set as a specific part is divided into grid-like small regions, and a blood flow variation is expressed by a change in hue for each small region.

The display information determination unit 113 determines a display range to set a color corresponding to a value of a luminance of a green signal. The display information determination unit 113 of the embodiment determines the display range based on a comparison result of the first pulse wave information before the specific action and the second pulse wave information after the specific action. The display information determination unit 113 selects a display method for emphasizing the degree of a color change in the hue moving image after the specific action as the degree of a change from the first pulse wave information to the second pulse wave information increases.

The image generation unit 114 generates a hue moving image based on a color map in which the display range determined by the display information determination unit 113 is set. Note that an example of a method for determining the display range will be described later. As illustrated in FIGS. 6A and 6B, a color corresponding to a luminance value of a green signal of each small region at a certain time is displayed in the hue moving image. Since the luminance of the green signal changes depending on the blood flow, a color displayed in each small region also changes with time. The image generation unit 114 generates an image in which a color corresponding to a luminance value is set in each region at a certain time. When the images thus generated are made temporally continuous, the hue moving image in which the colors change in a mosaic pattern is generated.

The image generation unit 114 generates a first hue moving image based on a measurement result of the first image and a second hue moving image based on a measurement result of the second image. Then, the image generation unit 114 combines the first hue moving image with the first image and combines the hue moving image based on the second measurement result with the second image. For example, when a specific part of the user is the face and a hue moving image is superimposed on the entire face, a combined image as illustrated in FIG. 6A or 6B is generated. A comparative image can be generated by displaying the combined image illustrated in FIG. 6A and the combined image illustrated in FIG. 6B side by side.

Figure 7:
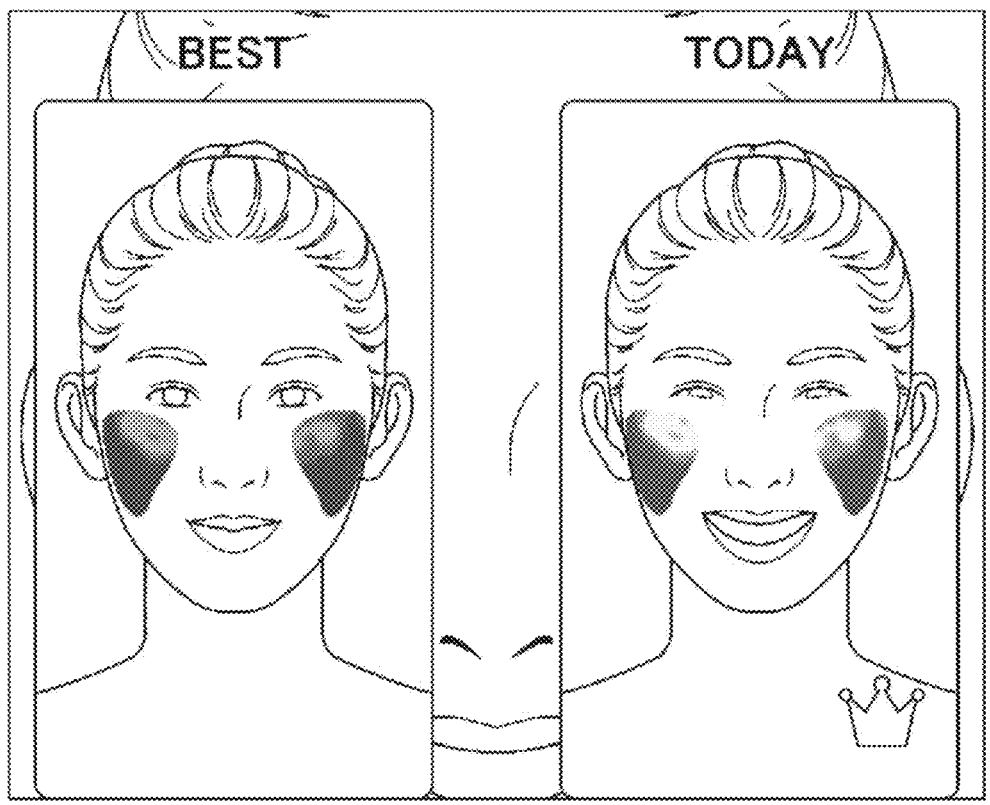
FIG. 7 is a view illustrating an example of an image illustrating a measurement result generated by the electronic device according to the embodiment of the invention.

The image generation unit 114 can also generate a measurement result image that displays both the past measurement result and the latest measurement result. FIG. 7 illustrates an example of the image illustrating the measurement result. On the left side of FIG. 7, a combined image of the user when the best massage (specific action) has been performed among the past measurement results is illustrated. On the right side, a combined image illustrating a measurement result of today's massage. In the example of FIG. 7, a hue moving image is combined with the cheek part of a user's image (actual image). As a result, the electronic device 1 of the embodiment can refer to the result of the specific action such as the past massage, and determine whether the specific action such as the massage performed this time has been appropriately performed.

The image generation unit 114 also performs a combining process of combining a guide image and an avatar image. The image generation unit 114 combines the guide image stored in the guidance information storage unit 191 and the avatar image stored in the avatar information storage unit 192 to generate an image in which the avatar image is combined with the guide image. The image generation unit 114 generates the combined image such that the guide image is superimposed on a predetermined part region such as the face of the avatar image. When guidance regarding a massage is performed, a combined image is generated such that a guide image of an arrow indicating movement of a hand during the massage is superimposed on a target part region to be massaged.

The display control unit 115 causes the display unit 18 to display a mirror image of the user or an image (for example, an avatar) corresponding to the user. In addition, a process of switching the display is performed based on display timings of various images and the user's operation on the input unit 17. The display control unit 115 determines a timing to display the combined image in which the image is combined with the hue moving image on the display unit 18. The timing when the display control unit 115 displays the hue moving image will be described later.

Further, the display control unit 115 executes a process of switching between a first display mode of mainly displaying the user image as the main image and displaying the combined image obtained by combining the avatar image and the guide image as a sub, and a second display mode of displaying the user image as a sub and mainly displaying the combined image obtained by combining the avatar image and the guide image. As illustrated in FIG. 2, the combined image of the avatar image and the guide image can be mainly displayed in a large size at the center of a screen, and the user image can be displayed as the sub at the bottom of the screen in a smaller size than the main image. On the contrary, the user image can be mainly displayed in a large size in the center of the screen, and the combined image of the avatar image and the guide image can be displayed as the sub at the bottom of the screen in a smaller size than the main image.

In addition, the display control unit 115 may automatically arrange and display a direction in which the user needs to face, a massage method, and biometric information as images or texts in a series of guidance in a region that does not overlap with the face of the user's mirror image or the face of the avatar image. Note that the display control unit 115 may output guidance information by another method in addition to the display. For example, the display control unit 115 may read the guidance information including sound data, and output a voice or music generated from the read guidance information from a speaker. In addition, for example, the display control unit 115 may change a light emitting state of the light emitting unit.

[Measurement Process]

Figure 8:
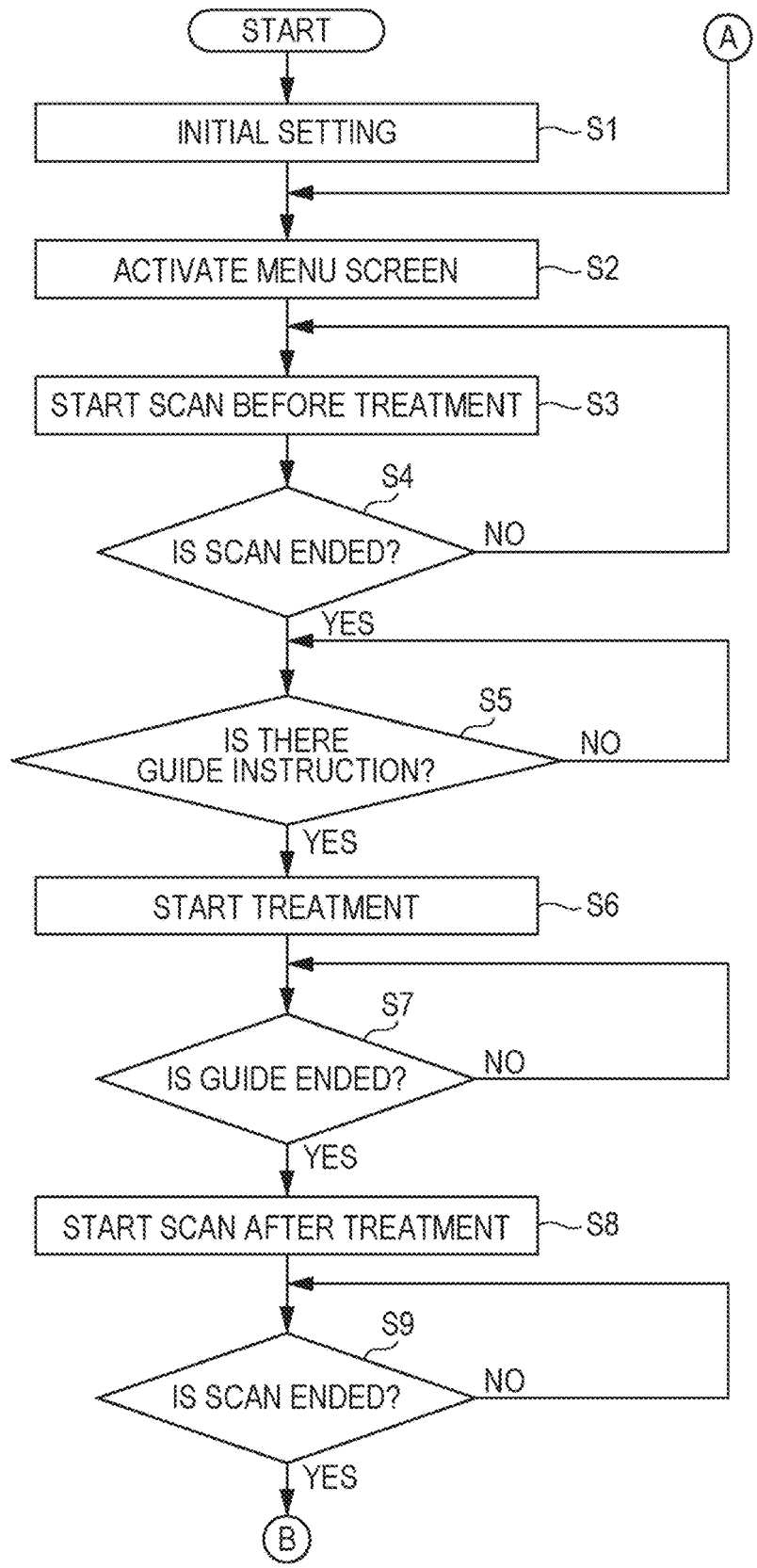
FIG. 8 is a flowchart illustrating a first half of the measurement process executed by the electronic device according to the embodiment of the invention.
Figure 9:
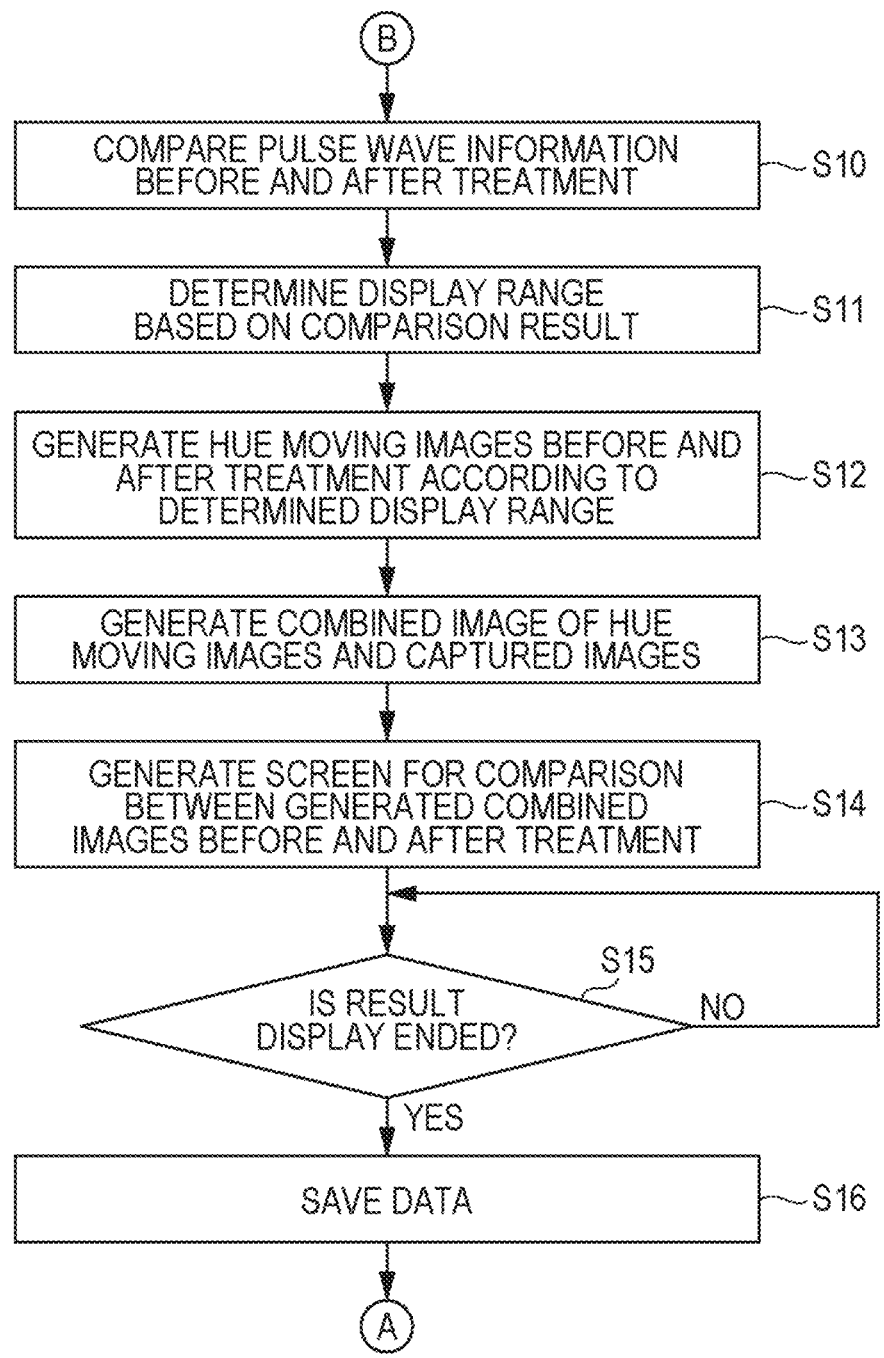
FIG. 9 is a flowchart illustrating a latter half of the measurement process executed by the electronic device according to the embodiment of the invention.

FIGS. 8 and 9 are flowcharts illustrating the overall flow of the measurement process executed by the electronic device 1 of FIG. 1 having the functional configuration of FIG. 5.

As illustrated in FIG. 8, the setting processing unit 111 performs initial setting in step S1. For example, the setting processing unit 111 downloads personal data set for each user ID from the authentication server included in the server group 3.

In step S2, the display control unit 115 performs an activation process of displaying a menu screen on the display unit 18.

In step S3, the information acquisition unit 112 starts imaging of the user using the imaging unit 16 in order to execute skin tracking and vital scan before treatment for the user before the treatment. Then, the imaging unit 16 analyzes the first image of the user. With this image analysis, biometric information of the user before the treatment is acquired. The biometric information includes information indicating a pulse wave of the user's face before the treatment, information indicating a temporal change in luminance of a green signal per small region for generation of a hue moving image (first pulse wave information), and the like. Note that step S3 may be automatically started after the activation of the menu screen is started, or may be started by receiving the user's operation on the input unit 17.

In step S4, the information acquisition unit 112 identifies a part such as the user's face and determines whether the biometric information has been appropriately acquired. When it is difficult to identify the part such as the user's face or the biometric information has not been appropriately acquired, it is determined as No in step S4, and the information acquisition unit 112 returns to step S3 and starts imaging using the imaging unit 16 again to analyze an image. When the part such as the user's face has been identified and the biometric information has been appropriately acquired, it is determined as Yes in step S4, and the process proceeds to step S5.

In step S5, the display control unit 115 determines whether a preset guide instruction for a specific action such as a massage has been received. Examples of the specific action include beauty treatment such as smile training, facial beauty treatment, relaxation (acupoint pressing and deep breathing), and a massage. In step S5, it is determined as No until the guide instruction is received by the user's operation on the input unit 17. If the guide instruction is received, it is determined as Yes in step S5, the display control unit 115 reads data necessary for giving guidance in response to the received guide instruction from the guidance information storage unit 191 and the avatar information storage unit 192, and the process proceeds to step S6.

In step S6, the image generation unit 114 and the display control unit 115 execute a process of generating a combined image based on the data read in step S6 by the user to start the treatment and displaying the combined image on the display unit 18. More specifically, a combined image on which an avatar image and a guide image illustrating movement of a hand in a massage during the facial beauty treatment have been superimposed is displayed. The user performs the massage in the facial beauty treatment while referring to this combined image. Alternatively, a combined image in which an avatar image and a guide image indicating a position of a first acupoint to be pressed have been superimposed is displayed. The user presses the user's own acupoint while referring to this combined image.

In step S7, the display control unit 115 determines whether to end a series of guidance. To determine whether the guidance has been completed, for example, whether the series of guidance has been completed may be determined based on biometric information, whether the user's specific action has been completed may be determined based on the image analysis, or the determination may be made based on the completion of the display of the guide image of the series of guidance. After a guidance process ends, the process proceeds to step S8.

In step S8, the information acquisition unit 112 analyzes the second image obtained by imaging the user after the treatment using the imaging unit 16 in order to execute vital scan after the treatment for the user after the treatment. The information acquisition unit 112 acquires biometric information after the specific action by analyzing the second image. The biometric information includes information indicating a pulse wave of the user's face after the treatment, information indicating a temporal change in luminance of a green signal per small region for generation of a hue moving image (second pulse wave information), and the like.

In step S9, the information acquisition unit 112 determines whether the biometric information has been appropriately acquired. When the biometric information has not been appropriately acquired, it is determined No in step S9, and the process of step S8 is executed again. When the biometric information has been appropriately acquired, the process proceeds to step S10.

As illustrated in FIG. 9, in step S10, the display information determination unit 113 executes a process of comparing the first pulse wave information indicating the pulse wave of the user before the treatment, and the second pulse wave information indicating the pulse wave of the user after the treatment. In this comparison process, the degree of a change between the first pulse wave information and the second pulse wave information is acquired as a comparison result.

In step S11, the display information determination unit 113 determines a display range when displaying a hue moving image based on the comparison result in step S9. The display range is determined for each of a hue moving image illustrating a state before the treatment and a hue moving image illustrating a state after the treatment.

In step S12, the image generation unit 114 generates the hue moving image before the treatment and the hue moving image after the treatment based on the respective display ranges determined in step S11. The first hue moving image illustrating the state of the user before the treatment is generated based on information indicating a temporal change of a luminance of a green signal per small region included in the first pulse wave information, and the second hue moving image illustrating the state of the user after the treatment is generated based on information indicating a temporal change of a luminance of a green signal per small region included in the second pulse wave information. Note that a process of determining the display range will be described later.

In step S13, the image generation unit 114 performs a superimposition process of combining the hue moving image with the image. For example, the image generation unit 114 detects the face as a predetermined part region of the user from the image captured by the imaging unit 16 by face tracking. Then, coordinates of the display unit coordinate system corresponding to coordinates of the detected part region in the imaging coordinate system are acquired based on the above-described correspondence between the coordinate systems. The display control unit 115 performs the superimposition process of displaying the hue moving image at the coordinates of the display unit coordinate system of the display unit 18.

In step S14, a comparative image that simultaneously displays the hue moving images whose time axes are different is generated. A comparative image displaying both the combined image before the treatment (for example, FIG. 6A) and the combined image after the treatment (for example, FIG. 6B), or a comparative image displaying both the past combined image and the current combined image as illustrated in FIG. 7 may be generated.

In step S15, the display control unit 115 stands by for a display end instruction of a comparison screen from the user. Notification of the display end instruction is provided by operating the input unit 17, for example. When the notification of the display end instruction is provided, the display control unit 115 ends the display of the comparative moving image, and the process proceeds to step S16.

In step S16, the information acquisition unit 112 stores data such as biometric information acquired by a series of measurement processes in the measurement result storage unit 193. After the end of step S16, the process returns to step S2, and the processes in step S2 and the subsequent steps are executed again.

[Display Information Determination Process]

Next, a display range determination process for adjusting the display of the display image will be described. The display information determination unit 113 has a color map that serves as a reference for displaying a display image. A display method of this color map changes depending on the display range to be described later. As illustrated in FIGS. 10, 12, and 14A to 14C, the color map is hue information for determination of a color corresponding to a luminance value. As the color map, for example, a jet color map can be used.

In the following description, scales of 0 to 9 are set in the color map for convenience of description, and a hue range is defined based on the scales. The scale 0 is set as the lowest coordinate in the color map, and the scale 9 is set as the highest coordinate in the color map. The low coordinate side has a blue (cold color) hue, and the high coordinate side has a red (warm color) hue. Further, a center coordinate of the color map is set at the middle between the scales 4 and 5.

[First Setting Process]

Figure 10:
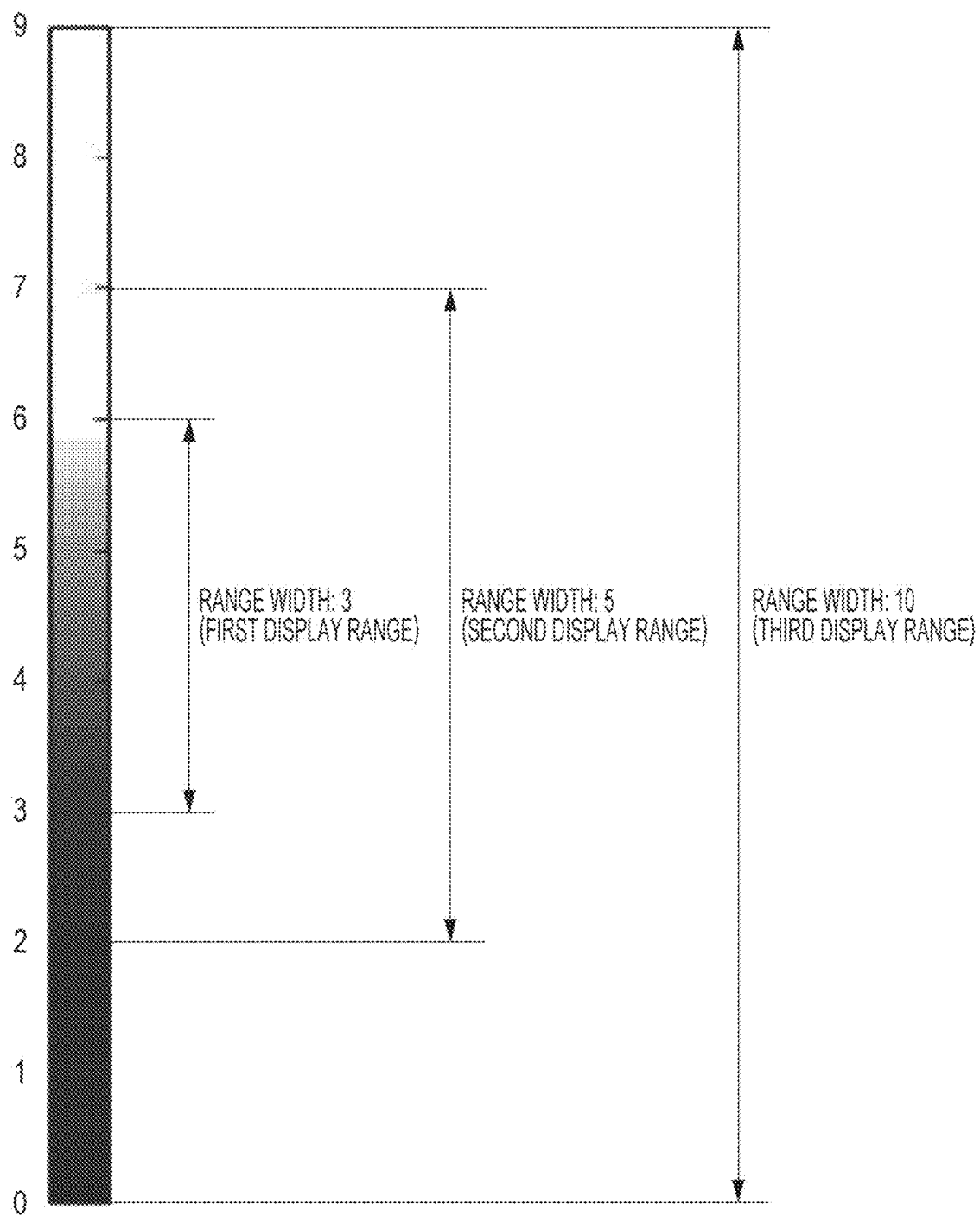
FIG. 10 is a schematic view illustrating a display range in a first setting process of the electronic device according to the embodiment of the invention.

As illustrated in FIG. 10, a display range in a first setting process is a setting value that specifies a range width of the color map. In the first setting process, three types, that is, a first display range, a second display range, and a third display range are set as the setting values that specify the range of the color map.

If the maximum range width of the color map is 10 from 0 to 9, the first display range is a setting value that has a range width between the scales 3 to 6 and specifies the narrowest range (range width 3). The first display range is set as a display range of the color map when the degree of the change from the first pulse wave information to the second pulse wave information is small, a negative change is made, there is no change, or the like.

The second display range is a setting value that has a range width of the scales 2 to 7 and specifies a medium range (range width 5). The second display range is set as a display range of the color map when the degree of the change from the first pulse wave information to the second pulse wave information is medium.

The third display range is a setting value that has a range width of the scales 0 to 9 and specifies the widest range (range width 10). The third display range is set as a display range of the color map when the degree of the change from the first pulse wave information to the second pulse wave information is large.

Figure 11:
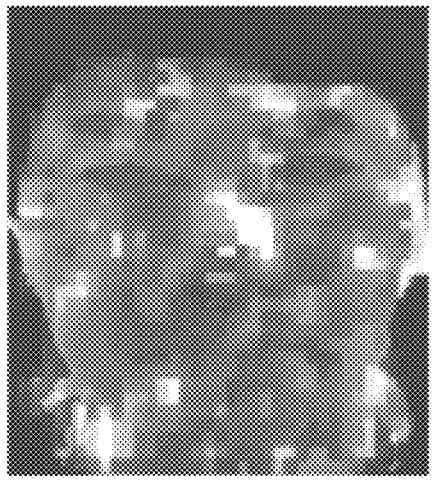
FIG. 11 is a view illustrating an example of a hue moving image generated based on the display range determined in the first setting process of the electronic device according to the embodiment of the invention.
Figure 11:
Figure 11:
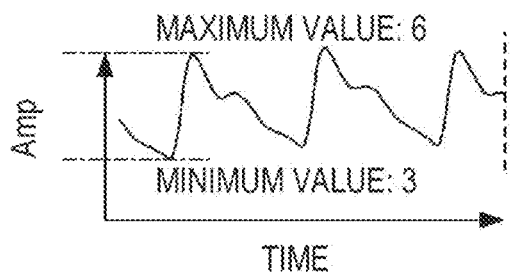
Figure 11:
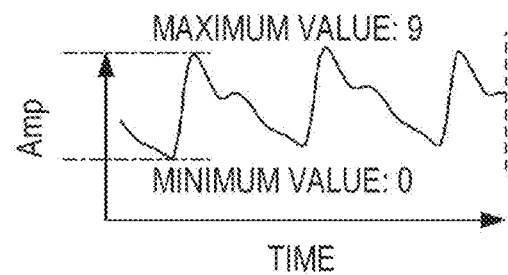

A hue moving image which illustrates a blood flow of the user before a specific action and in which the first display range of the range width 3 has been set is illustrated on the left side of FIG. 11. On the other hand, a hue moving image which illustrates a blood flow of the user after a specific action and in which the third display range of the range width 10 has been set is illustrated on the right side of FIG. 11. FIG. 11 also illustrates that it is possible to implement the display in which a blood flow variation can be intuitively grasped by changing the range width according to the degree of the blood flow variation before and after the specific action.

In the first setting process, the image generation unit 114 sets a color to be displayed in each region such that a positive peak of an amplitude corresponds to the maximum value of the range width and a negative peak of an amplitude corresponds to the minimum value of the range width in a pulse wave of the luminance in the small regions. For example, in the first display range, the scale 6 of the color map corresponds to the positive peak of the pulse wave, and the scale 3 corresponds to the negative peak of the pulse wave. In the second display range, the scale 7 of the color map corresponds to the positive peak of the pulse wave, and the scale 2 corresponds to the negative peak of the pulse wave. In the third display range, the scale 9 of the color map corresponds to the positive peak of the pulse wave, and the scale 0 corresponds to the negative peak of the pulse wave.

[Second Setting Process]

Figure 12:
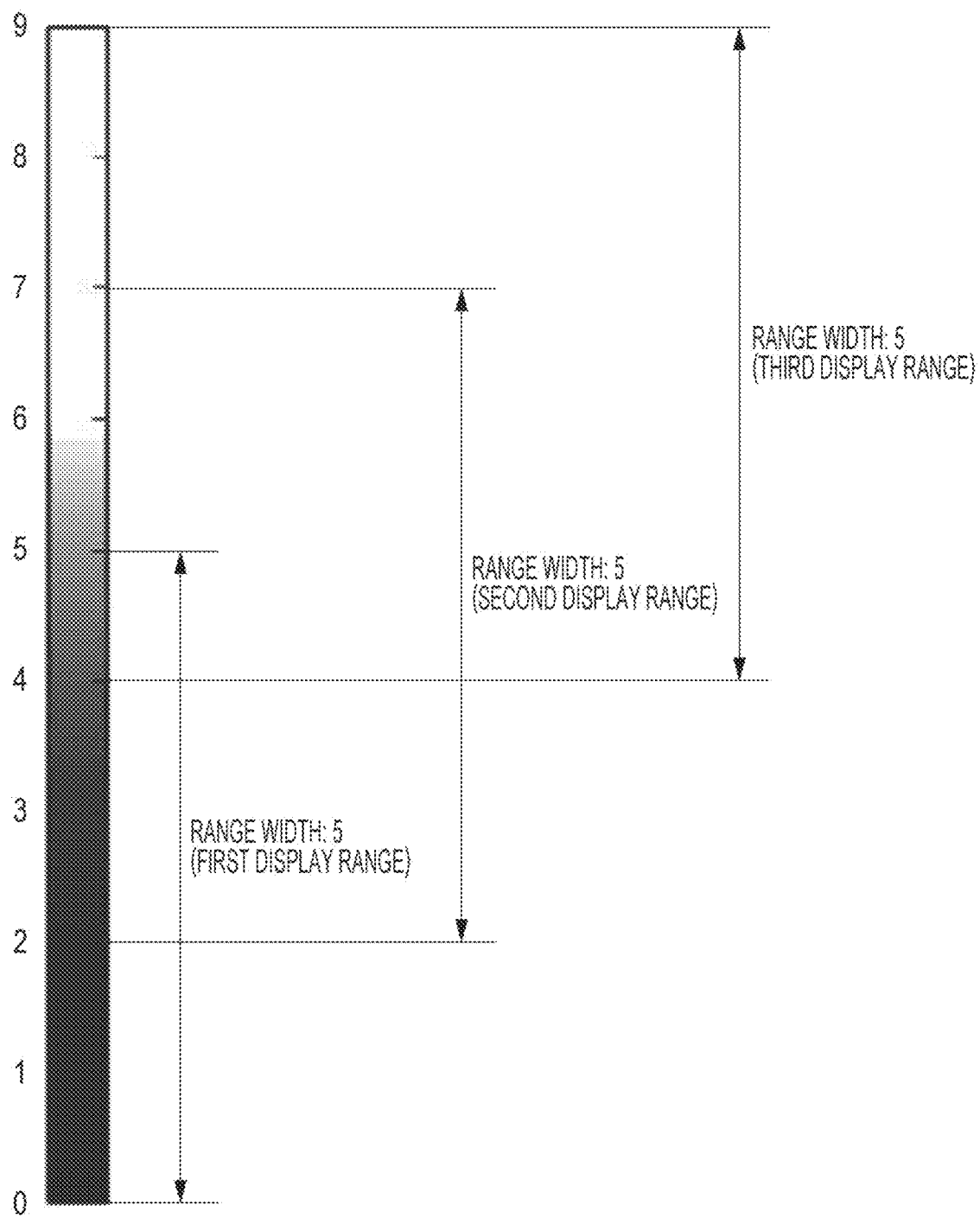
FIG. 12 is a schematic view illustrating a display range in a second setting process of the electronic device according to the embodiment of the invention.

Next, a second setting process different from the first setting process will be described. As illustrated in FIG. 12, three range widths of a first display range, a second display range, and a third display range are specified even in the second setting process. The first display range is a range having a range width of the scales 0 to 5 (range width 5), the second display range is a range having a range width of the scales 2 to 7 (range width 5), and the third display range is a range having a range width of the scales 4 to 9 (range width 5). That is, the first display range is the range located on the low coordinate side, the second display range is a range located on the center side centered on the center coordinate, and the third display range is a range located on the high coordinate side. In this example, the first display range, the second display range, and the third display range have the same range length, but are set at misaligned positions (coordinates).

Figure 13:
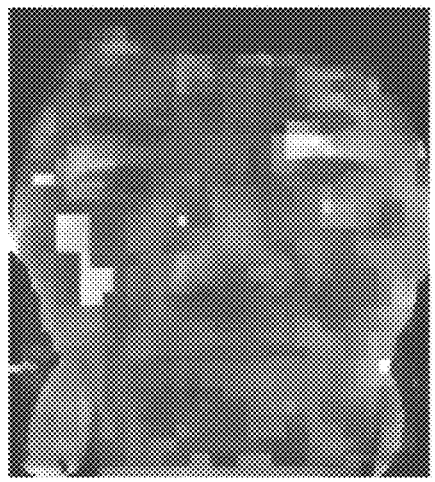
FIG. 13 is a view illustrating an example of a hue moving image generated based on the display range determined in the second setting process of the electronic device according to the embodiment of the invention.
Figure 13:
Figure 13:
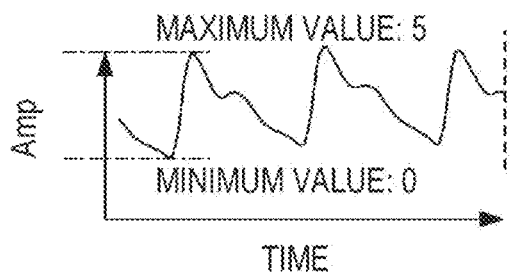
Figure 13:
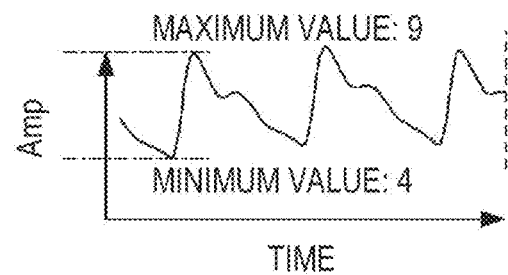

A hue moving image which illustrates a blood flow of the user before a specific action and in which the first display range located on the low coordinate side has been set is illustrated on the left side of FIG. 13. On the other hand, a hue moving image which illustrates a blood flow of the user after a specific action and in which the third display range located on the high coordinate side has been set is illustrated on the right side of FIG. 13. FIG. 13 also illustrates that it is possible to implement the display in which a blood flow variation can be intuitively grasped by changing coordinates of the range width according to the degree of the blood flow variation before and after the specific action.

Even in the second setting process, the image generation unit 114 sets a color to be displayed in each region such that a positive peak of an amplitude corresponds to the maximum value of the range width and a negative peak of an amplitude corresponds to the minimum value of the range width in a pulse wave of the luminance in the small regions. For example, in the first display range, the scale 5 of the color map corresponds to the positive peak of the pulse wave, and the scale 0 corresponds to the negative peak of the pulse wave. In the second display range, the scale 7 of the color map corresponds to the positive peak of the pulse wave, and the scale 2 corresponds to the negative peak of the pulse wave. In the third display range, the scale 9 of the color map corresponds to the positive peak of the pulse wave, and the scale 4 corresponds to the negative peak of the pulse wave.

[Third Setting Process]

Figure 14A:
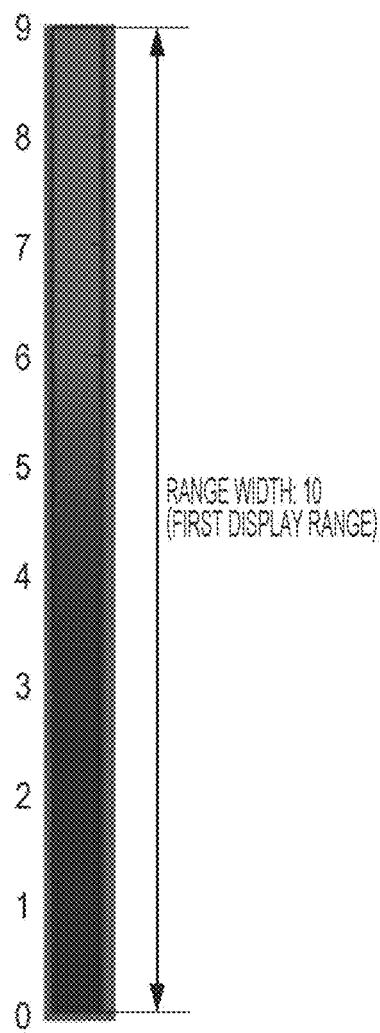
FIGS. 14A to 14C are schematic views illustrating display ranges in a third setting process of the electronic device according to the embodiment of the invention.
Figure 14B:
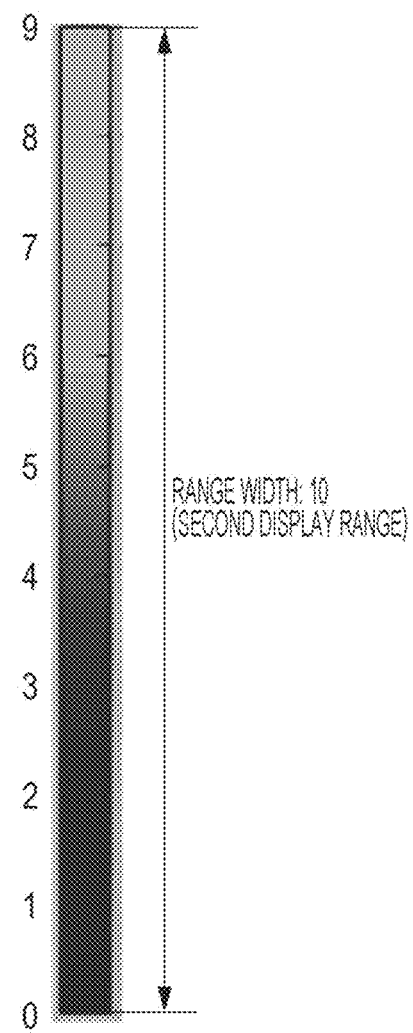
Figure 14C:
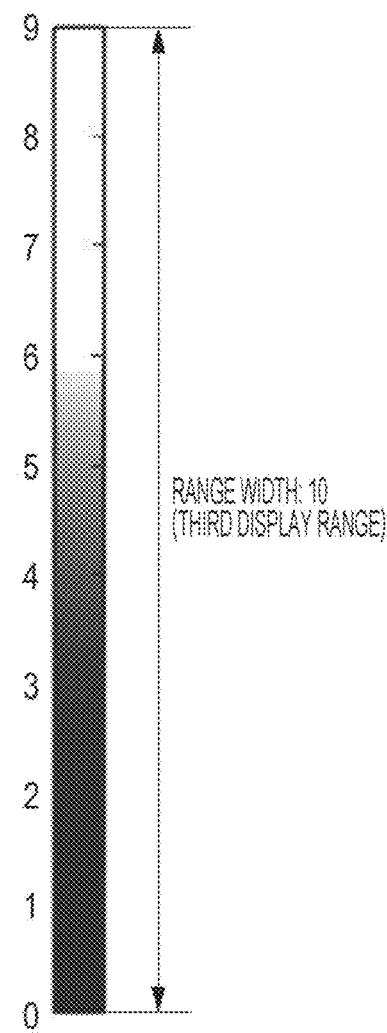

Next, a third setting process different from the first setting process and the second setting process will be described. As illustrated in FIGS. 14A to 14C, a setting value of a display luminance of the color map set in the color map is changed in the third setting process. That is, the display information determination unit 113 adjusts a luminance of a color to be displayed according to the degree of the change from the first pulse wave information to the second pulse wave information.

FIG. 14A is a color map in which the darkest luminance is set as a first display range. Similarly, FIG. 14B is a color map in which the medium luminance is set as a second display range. FIG. 14C is a color map in which the brightest luminance is set as a third display range. As illustrated in FIGS. 14A to 14C, range widths of the first display range, the second display range, and the third display range in the third setting process are all set to the same 10.

Figure 15:
FIG. 15 is a view illustrating an example of a hue moving image generated based on the display range determined in the third setting process of the electronic device according to the embodiment of the invention.
Figure 15:
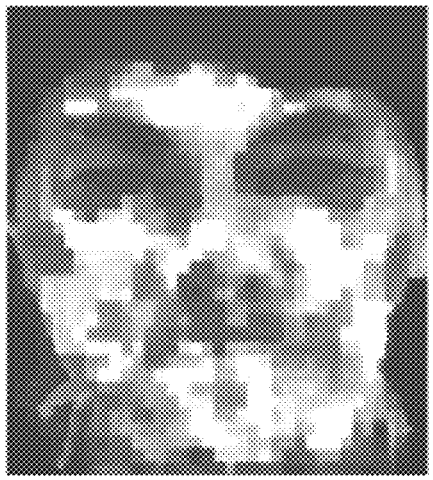
Figure 15:
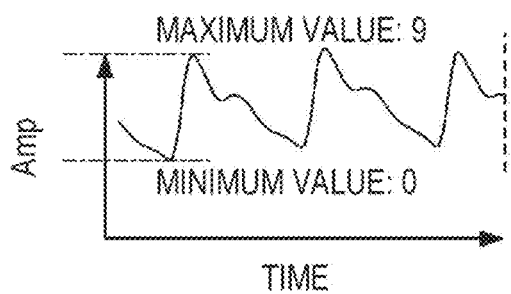
Figure 15:
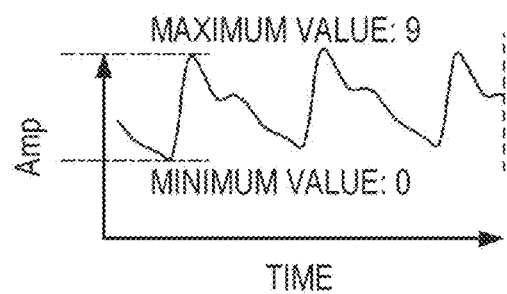

A hue moving image which illustrates a blood flow of the user before a specific action and in which the first display range set with the low luminance has been set is illustrated on the left side of FIG. 15. On the other hand, a hue moving image which illustrates a blood flow of the user after a specific action and in which the third display range set with the high luminance has been set is illustrated on the right side of FIG. 15. FIG. 15 also illustrates that it is possible to implement the display in which a blood flow variation can be intuitively grasped by changing the luminance of the hue according to the degree of the blood flow variation before and after the specific action.

Even in the third setting process, the image generation unit 114 sets a color to be displayed in each region such that a positive peak of an amplitude corresponds to the maximum value of the range width and a negative peak of an amplitude corresponds to the minimum value of the range width in a pulse wave of the luminance in the small regions. In any of the first display range, the second display range, and the third display range, the scale 9 of the color map corresponds to the positive peak of the pulse wave, and the scale 0 corresponds to the negative peak of the pulse wave.

Although the adjustment of display information to set the display image using the color map has been described as above by taking the first setting process, the second setting process, and the third setting process as examples, the display information setting process is not limited to these methods. For example, the first setting process may be combined with the second setting process and the third setting process, the second setting process may be combined with the third setting process, or all of the first to third setting processes may be combined.

[Description of Comparison Process]

Next, an example of the comparison process of comparing the degree of the change from the first pulse wave information to the second pulse wave information will be described. Since the amount of hemoglobin per unit time increases when the blood flow rises, more green signals are absorbed by hemoglobin than before the rise of the blood flow. Therefore, the luminance of the green signal detected during the rise of the blood flow decreases. In the embodiment, a conversion process is performed such that the luminance value increases as the blood flow rises in order to make it easier to sensually grasp the rise of the blood flow. More specifically, when the luminance of the green signal is detected using an image sensor that outputs 8-bit RGB colors, a numerical value obtained by subtracting a luminance value of the detected green signal from the maximum value 255 of the luminance value is used as the "converted luminance value" in the comparison process. Hereinafter, what is simply described as the converted luminance value is information on the luminance that has been subjected to such a conversion process. A display range determined based on the result of the comparison process is set using any of the above-described first setting process, second setting process, and third setting process.

[First Comparison Process]

Figure 16:
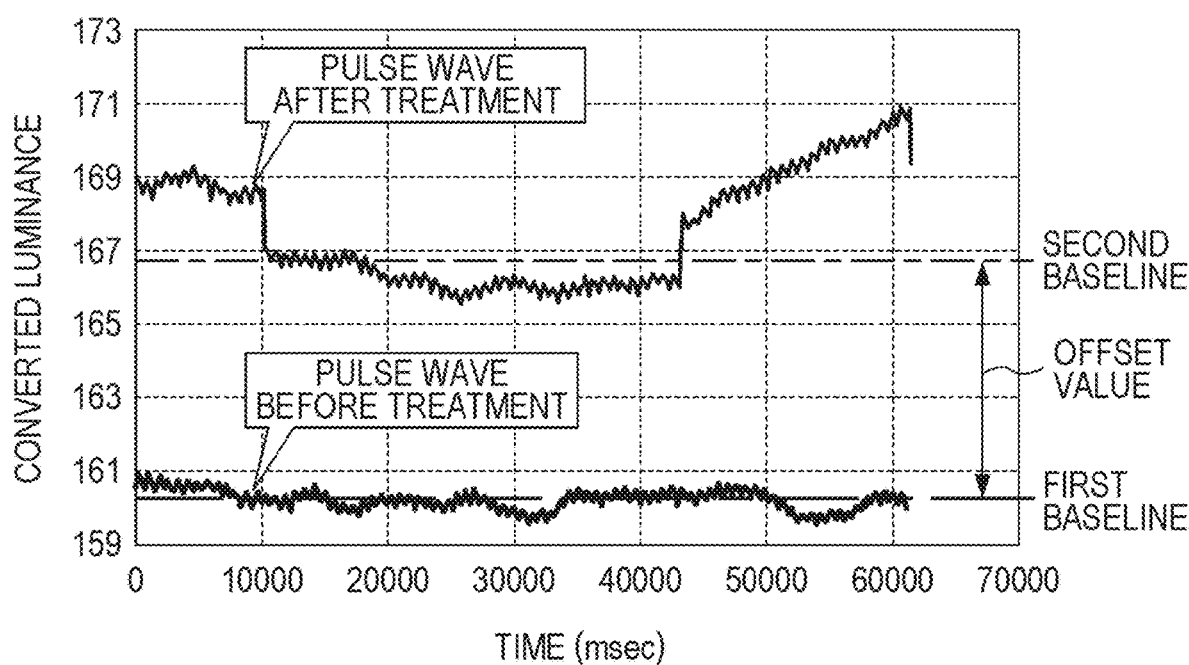
FIG. 16 is a graph illustrating examples of first pulse wave information and second pulse wave information acquired by the electronic device according to the embodiment of the invention.

As illustrated in FIG. 16, a blood flow rate of the entire face increases with the passage of time as the user performs a specific action such as a facial cheek treatment (for example, a massage), and thus, an average luminance value of waveforms of the pulse wave tends to be different when comparing before and after the treatment. The average luminance value is a numerical value based on the converted luminance value. In the first comparison process, a display range is determined by paying attention to the change in the pulse wave after this specific action. Note that the pulse wave information used in the first comparison process and the pulse wave information (first pulse wave information and second pulse wave information) illustrated in FIG. 16 are obtained by calculating an average value of luminances of the entire part set as the region of interest for each predetermined time (for example, the time when a plurality of pulse wave waveforms of about several seconds are included).

The display information determination unit 113 calculates a first baseline indicating an average value of the first pulse wave information indicating the pulse wave before the treatment for a predetermined time. The first baseline is a straight broken line in the graph of FIG. 16. Similarly, the display information determination unit 113 calculates a second baseline indicating an average value of the second pulse wave information for a predetermined time. The second baseline is a straight one-dot chain line in the graph of FIG. 16.

It is preferable that a range (time) of the pulse wave at the time of calculating the first baseline be set in a region where the pulse wave is stable. For example, when an abnormal value exceeding a preset threshold is detected, the pulse wave information is acquired to exclude the abnormal value. Alternatively, a fact that an image has not been appropriately acquired at the time of imaging may be displayed, and reimaging may be performed to acquire appropriate pulse wave information. Alternatively, a pulse wave after a lapse of a predetermined time since the start of imaging may be used to calculate the baseline. Alternatively, the baseline may be calculated by removing an abnormal value from a pulse wave acquired within a predetermined time. In this manner, various methods can be applied for the calculation of the baseline.

Next, the display information determination unit 113 acquires an offset value indicating a difference between the first baseline and the second baseline as a comparison result. A display range is set based on this offset value. In the above-described setting process, any one of the first display range, the second display range, and the third display range is set as the display range based on the offset value.

The display range is set with the offset value of 0 at the time of generating a hue moving image before a specific action In this example, the first display range is the display range of the hue moving image before the specific action.

The display range is determined based on the difference between the first baseline and the second baseline at the time of generating a hue moving image after the specific action. A reference value of the offset value to determine the display range is appropriately set, and the display range is determined by comparing the offset value and the reference value. It suffices that the reference value is a numerical value that allows the user to visually distinguish a difference when comparing a hue moving image in the case of exceeding the reference value and a hue moving image in the case of not exceeding the reference value, and the reference value is determined by experiments conducted for the user or theoretical values that lead to visual conditions. When there are a plurality of display ranges to be selected, such as the first display range, the second display range, and the third display range, a plurality of reference values are also set stepwise such as a first reference value and a second reference value. For example, the first reference value is set to 3 and the second reference value is set to 6 in consideration of the range of the color map. In this setting, the first display range is set when the difference between the first baseline and the second baseline is "offset value≤3", the second display range is set when "3<offset value<6", and the third display range is set when "offset value≥6". Note that the offset value is sometimes negative depending on a situation. For example, there is a case where a first image is acquired by imaging a state where a blood flow rises immediately after bathing when the user takes a bath, and a second image is acquired by imaging a state where the blood flow has decreased after a lapse of time since the acquisition of the first image. In this case, the offset value is negative, and thus, it is determined as the case where "offset value≤3", and a process of setting the first display range may be performed or a process of displaying a message indicating that the measurement has not been appropriately performed may be performed.

[Second Comparison Process]

Next, a second comparison process of comparing the degree of the change from the first pulse wave information to the second pulse wave information by a different method from the first comparison process will be described. Note that the pulse wave information used in the second comparison process and the pulse wave information (first pulse wave information and second pulse wave information) illustrated in FIGS. 17A to 19B are obtained by calculating an average luminance value of the entire part set as the region of interest for each predetermined time (for example, the time when a plurality of pulse wave waveforms of about several seconds are included). The average luminance value is a numerical value based on the converted luminance value.

Figure 17A:
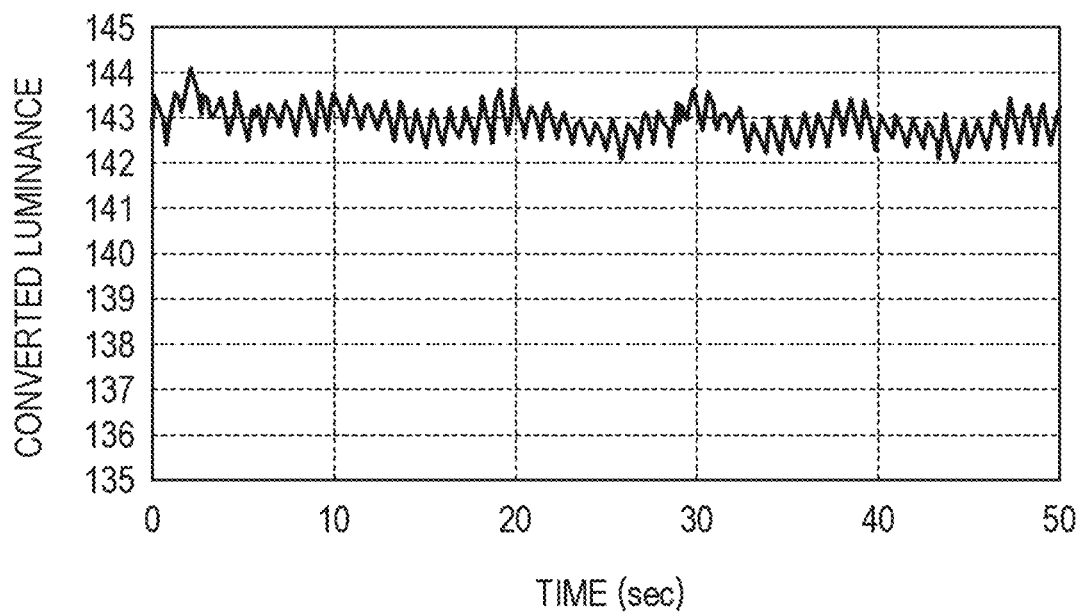
FIGS. 17A and 17B are graphs illustrating examples in which pulse wave information different depending on an orientation of a face is acquired.
Figure 17B:
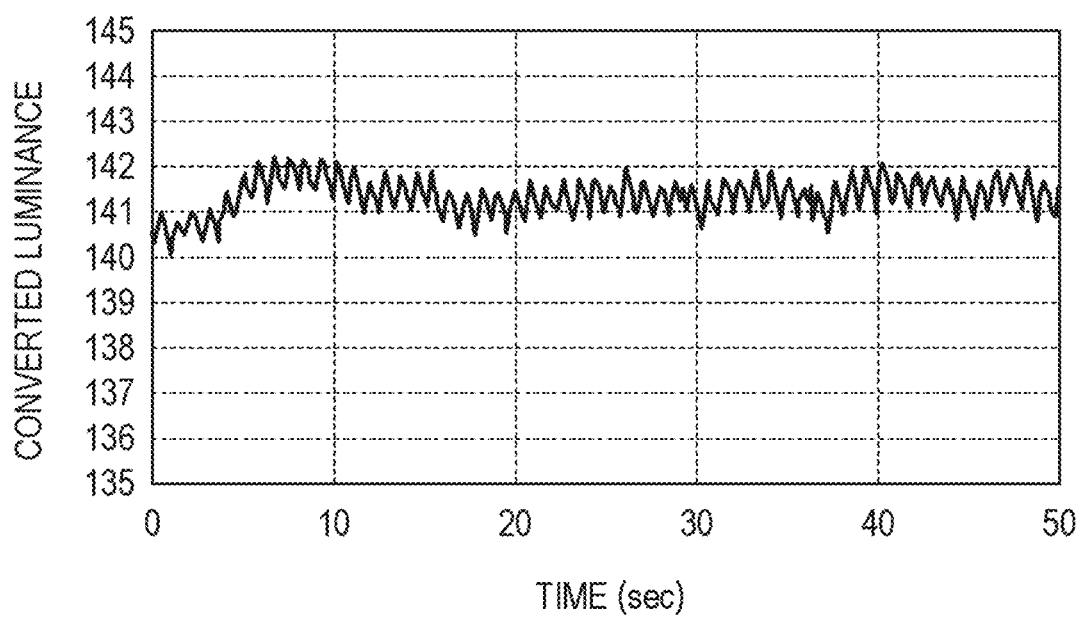

FIG. 17A is a graph of pulse wave information calculated based on an image in a state where the user is looking at the imaging unit 16 in a correct posture, and FIG. 17B is a graph of pulse wave information calculated based on an image in a state where the user's face is oriented slightly upward. In either case, the user does not take any specific action, and the environment such as an illumination during imaging is the same. When comparing FIGS. 17A and 17B, it can be understood that the overall luminance tends to be brighter in the state where the user's face is oriented slightly upward (darker as the converted luminance value is larger). It is considered that how the light hits the face affects the acquisition of the luminance of the green signal.

Since it is not always possible for the user to maintain the same posture with respect to the imaging unit 16 before and after a specific action, it is preferable to eliminate the influence of the face orientation. In the first comparison process, it is difficult to compare the first pulse wave information and the second pulse wave information by eliminating the influence of the face orientation. In this regard, the second comparison process employs a process that can eliminate the influence of a change in the face orientation. More specifically, after the specific action such as a massage, a blood flow increases, and a pulse wave amplitude increases (for example, by 10%). Therefore, the display information determination unit 113 that performs the second comparison process determines a display range based on an increase rate of the amplitude by paying attention to the increase in the amplitude of the pulse wave after the specific action, thereby eliminating the influence of the face orientation.

Figure 18A:
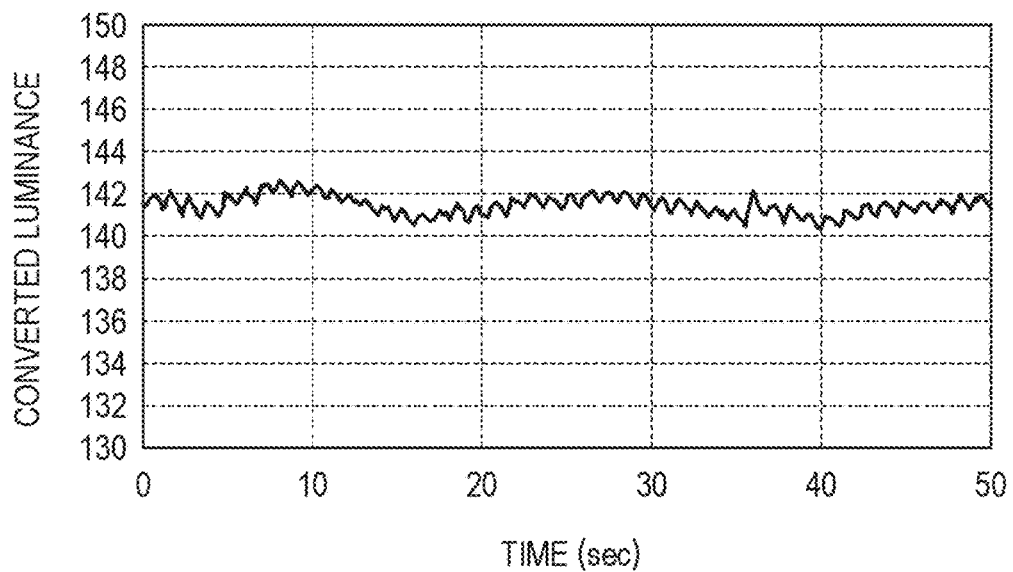
FIGS. 18A and 18B are graphs illustrating examples in which a first amplitude is acquired from the first pulse wave information by the electronic device according to the embodiment of the invention.
Figure 18B:
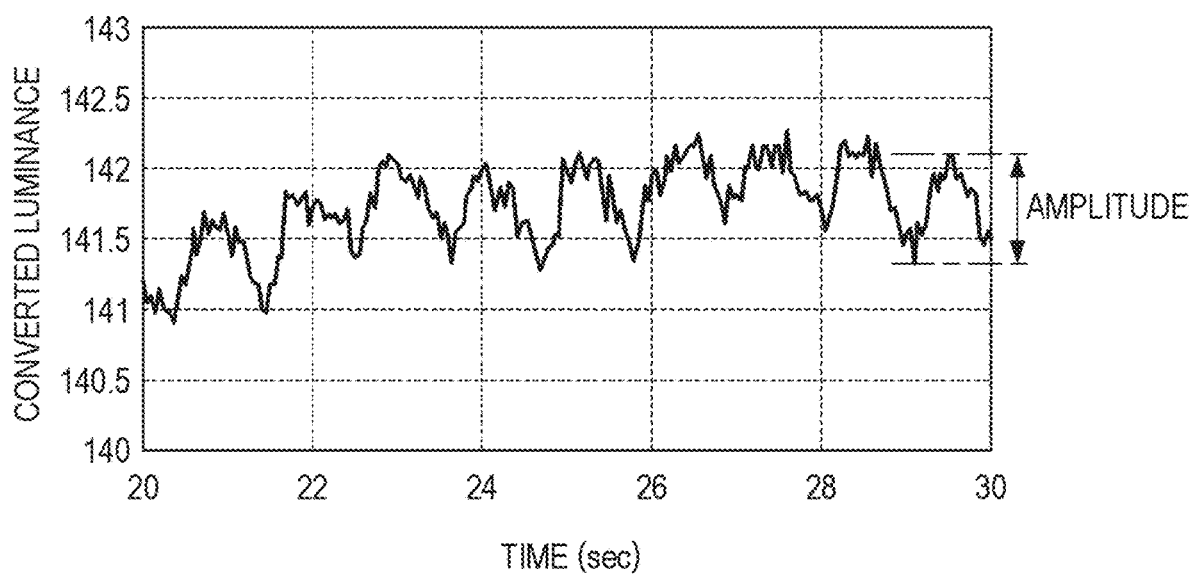

FIG. 18A is a graph illustrating the first pulse wave information before the specific action such as the massage, and FIG. 18B is a graph obtained by enlarging a part of the pulse wave information of FIG. 18A. The display information determination unit 113 identifies a range to acquire an amplitude from the first pulse wave information. The range to acquire the amplitude is a region where the amplitude is stable without any abnormal value. The display information determination unit 113 acquires first amplitude information indicating the amplitude of the pulse wave before the specific action based on a section average of the range or the like.

Figure 19A:
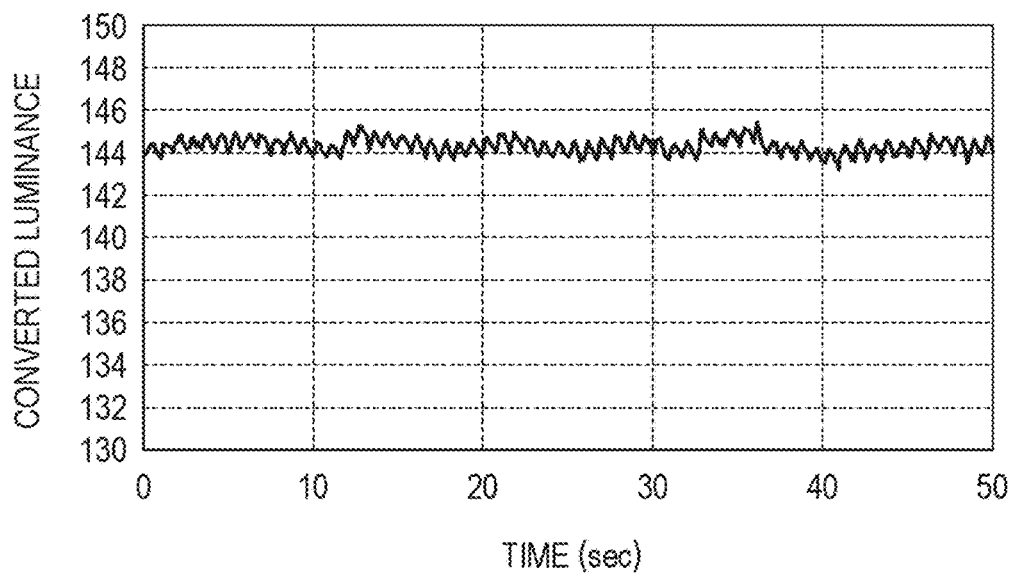
FIGS. 19A and 19B are graphs illustrating examples in which a second amplitude is acquired from the second pulse wave information by the electronic device according to the embodiment of the invention.
Figure 19B:
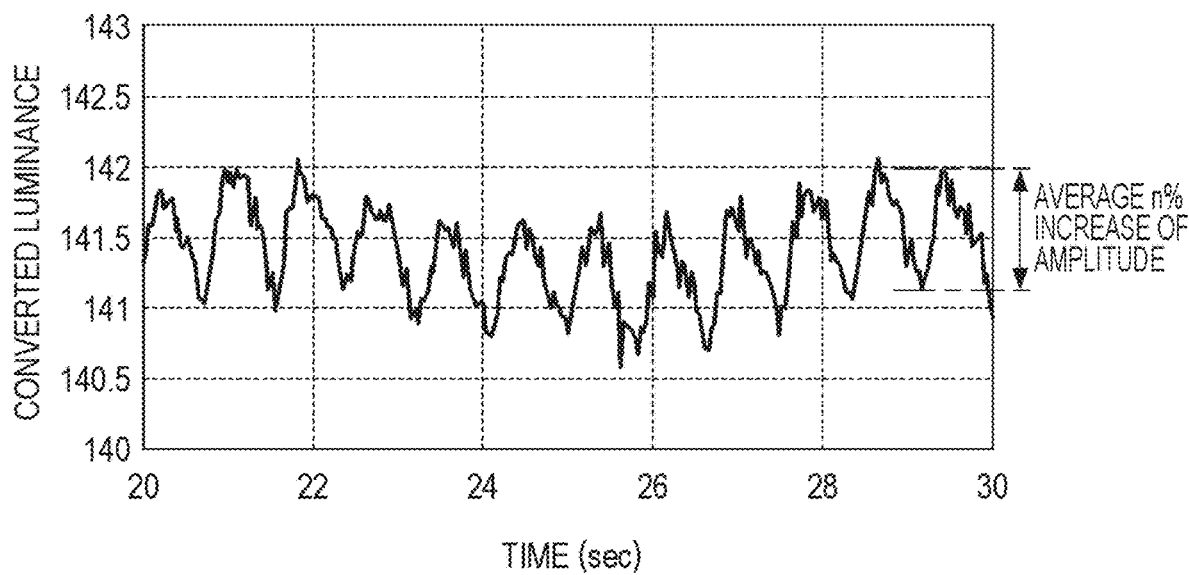

FIG. 19A is a graph illustrating the second pulse wave information after the specific action such as the massage, and FIG. 19B is a graph obtained by enlarging a part of the pulse wave information of FIG. 19A. The display information determination unit 113 identifies a range to acquire an amplitude from the second pulse wave information. The range to acquire the amplitude is a region where the amplitude is stable without any abnormal value. The display information determination unit 113 acquires second amplitude information indicating the amplitude of the pulse wave after the specific action based on a section average of the range or the like.

It is preferable that a range (time) of the pulse wave at the time of calculating the amplitude be set in a region where the pulse wave is stable. For example, when an abnormal value exceeding a preset threshold is detected, the pulse wave information is acquired to exclude the abnormal value. Alternatively, a fact that an image has not been appropriately acquired at the time of imaging may be displayed, and reimaging may be performed to acquire appropriate pulse wave information. Alternatively, a pulse wave after a lapse of a predetermined time since the start of imaging may be used to calculate the amplitude. Alternatively, the amplitude may be calculated by removing an abnormal value from a pulse wave acquired within a predetermined time. In this manner, various methods can be applied for the calculation of the amplitude.

The display information determination unit 113 determines a display range by comparing the first amplitude information and the second amplitude information. The pulse wave after the specific action such as the massage usually has a large amplitude because the blood flow has been improved. The display information determination unit 113 determines the display range based on the increase rate of the amplitude.

The display range is set with the increase rate of 0 at the time of generating a hue moving image before a specific action. In this example, the first display range is the display range of the hue moving image before the specific action.

The display range is determined based on the increase rate of the second amplitude information relative to the first amplitude information at the time of generating a hue moving image after the specific action. A reference value of the increase rate to determine the display range is appropriately set, and the display range is determined by comparing the increase rate and the reference value. It suffices that the reference value is a numerical value that allows the user to visually distinguish a difference when comparing a hue moving image in the case of exceeding the reference value and a hue moving image in the case of not exceeding the reference value, and the reference value is determined by experiments conducted for the user or theoretical values that lead to visual conditions. When there are a plurality of display ranges to be selected, such as the first display range, the second display range, and the third display range, a plurality of reference values are also set stepwise such as a first reference value and a second reference value. For example, when calculating the increase rate in percentage, a first reference value is set to a number larger than 100 (hereinafter, R1) in consideration of the range of the color map, and a second reference value is set to a number larger than R1 (hereinafter, referred to as R2). In this manner, under a condition that the relationship of 100<R2<R1 is established, the first display range is set when the result of comparing the first amplitude information and the second amplitude information is "increase rate≤R2", the second display range is set when "R2<increase rate<R1", and the third display range is set when "increase rate≥R1". Note that there is a case where the amplitude does not increase depending on a situation. For example, there is a case where a first image is acquired by imaging a state where a blood flow rises immediately after bathing when the user takes a bath, and a second image is acquired by imaging a state where the blood flow has decreased after a lapse of time since the acquisition of the first image. In this case, the increase rate is less than 100, and thus, it is determined as the case where "increase rate≤R2", and a process of setting the first display range may be performed or a process of displaying a message indicating that the measurement has not been appropriately performed may be performed.

The image generation unit 114 sets a color to be displayed in a small region at a certain time based on the display range determined by the comparison process described above and the color map. Note that the hue moving image displays changes in hue in the mosaic shape based on the temporal change of the luminance set per small region. Therefore, the hue moving image is not generated based on the first pulse wave information and the second pulse wave information, which are the average values of the entire specific part, but the hue moving image is generated based on the temporal change of the luminance acquired per small region.

The electronic device 1 according to the embodiment described above includes the information acquisition unit 112, the display information determination unit 113, and the display control unit 115. The information acquisition unit 112 acquires the first pulse wave information indicating the pulse wave of a part of the body of the user based on image information of the body in the first image obtained by imaging at least a specific part such as a face, which is the part of the body of the user, and acquires the second pulse wave information indicating the pulse wave of the part of the body based on image information of the body in the second image obtained by imaging the part of the body after a specific action after the first image has been obtained. The display information determination unit 113 determines the display range of the display color of the display image corresponding to the blood flow variation of the part of the body based on the first pulse wave information and the second pulse wave information. The display control unit 115 controls the display of the display image by the display color determined based on the display range determined by the display information determination unit 113 and the second pulse wave information.

As a result, it is possible to notify the user of the change in blood flow in two images with different time axes in an easy-to-understand manner. For example, even if the blood flow is improved as a result of the specific action, it is difficult to distinguish a difference before and after the specific action only by simply displaying the hue moving images in the same display range since the waveform of the pulse wave is displayed as the color map in the display in the embodiment. In this regard, with the configuration of the embodiment, the hue moving image can be generated by reflecting the degree of the change in blood flow after performing the specific action or the like, and thus, the measurement result can be displayed in an easy-to-understand manner due to a difference in tendency of the color to be displayed.

In the embodiment, the blood flow variation is a variation from the blood flow of the part of the body in the first image to the blood flow of the part of the body in the second image. As a result, it is possible to visually illustrate the change in blood flow with different time axes for the user.

In the embodiment, the display control unit 115 controls the display of the display image based on the second pulse wave information including information which is the difference between the peak and the bottom of the luminance corresponding to the pulse wave of the part of the body at the time of capturing the second image. As a result, as illustrated in the above-described embodiment, it is possible to generate the image by utilizing the temporal change of the average value of the luminance of the green signal of all the pixels in the region set as the region of interest.

In the embodiment, the display control unit 115 performs control to display the moving image as the display image. As a result, the blood flow variation can be dynamically visualized, and the difference between before and after the specific action can be displayed in an easy-to-understand manner In the embodiment, the information acquisition unit 112 acquires the first pulse wave information based on the first luminance information included in the image information of the body in the first image, and acquires the second pulse wave information based on the second luminance information included in the image information of the body in the second image. As a result, it is possible to generate the image visually representing the blood flow variation by utilizing the luminance of the green signal caused by hemoglobin.

In the embodiment, the first luminance information is information on the converted luminance value (luminance value) of at least one pixel in the part of the body in the first image or the average luminance of the entire region corresponding to the part of the body in the first image, and the second luminance information is information on the converted luminance value (luminance value) of one pixel in the part of the body in the second image or the average luminance of the entire region corresponding to the part of the body in the second image. As a result, it is possible to generate the image that visually illustrates the blood flow variation in a specific region.

In the embodiment, the display information determination unit 113 determines the display range of the display color based on the difference between the first pulse wave information and the second pulse wave information. As a result, the offset after the specific action such as the massage can be used, and the image that reflects the degree of the blood flow variation after the specific action can be generated without performing complicated processing.

As illustrated in the first comparison process, the display information determination unit 113 determines the display range of the display color based on the difference between the first baseline acquired based on the first pulse wave information and the second baseline acquired based on the second pulse wave information. As a result, it is possible to acquire the difference between the first pulse wave information and the second pulse wave information without performing complicated calculation processing.

In the embodiment, the first baseline is acquired based on the average value of converted luminance values (luminance values) corresponding to a pulse wave in a range where the pulse wave is stable in the first pulse wave information, and the second baseline is acquired based on the average value of converted luminance values (luminance values) corresponding to a pulse wave in a range where the pulse wave is stable in the second pulse wave information. As a result, it is possible to effectively prevent a situation where the converted luminance value (luminance value) that has not been normally detected is reflected in the display, and it is possible to more accurately visualize the actual blood flow variation.

As illustrated in the first setting process, the display information determination unit 113 sets the range width of the display range centered on the color corresponding to the center coordinate of the display range to be wider than the range width of the display range applied when the difference between the first pulse wave information and the second pulse wave information is relatively low as the difference between the first pulse wave information and the second pulse wave information increases, and sets the range width of the display range centered on the color corresponding to the center coordinate of the display range to be narrower than a range width of the display range applied when the difference between the first pulse wave information and the second pulse wave information is relatively high as the difference between the first pulse wave information and the second pulse wave information or the increase rate of the second amplitude relative to the first amplitude decreases (the first comparison process). Similarly, the display information determination unit 113 sets the range width of the display range centered on the color corresponding to the center coordinate of the display range to be wider than the range width of the display range applied when the increase rate of the second amplitude relative to the first amplitude is relatively low as the increase rate of the second amplitude relative to the first amplitude is higher, and sets the range width of the display range centered on the color corresponding to the center coordinate of the display range to be narrower than the range width of the display range applied when the increase rate of the second amplitude relative to the first amplitude is relatively high as the increase rate of the second amplitude relative to the first amplitude is lower (the second comparison process). As a result, the color changes in a narrow range when the degree of the change is small in the hue moving image, but the color changes dramatically when the degree of the change is large. Thus, the degree of the blood flow variation generated between the first image and the second image can be reflected in the display of the hue moving image in an easy-to-understand manner As illustrated in the second setting process, the display information determination unit 113 sets, as the display range, a range on the higher coordinate side of a range of the display range applied when the difference between the first pulse wave information and the second pulse wave information is relatively low among ranges of the display range as the difference between the first pulse wave information and the second pulse wave information increases, and sets, as the display range, a range on the lower coordinate side of a range of the display range applied when the difference between the first pulse wave information and the second pulse wave information is relatively high among the ranges of the display range as the difference between the first pulse wave information and the second pulse wave information decreases (the first comparison process). Similarly, the display information determination unit 113 sets, as the display range, a range on the higher coordinate side of a range of the display range applied when the increase rate of the second amplitude relative to the first amplitude is relatively low among the ranges of the display range as the increase rate of the second amplitude relative to the first amplitude is higher, and sets, as the display range, a range on the lower coordinate side of a range of the display range applied when the increase rate of the second amplitude relative to the first amplitude is relatively high among the ranges of the display range as the increase rate of the second amplitude relative to the first amplitude is lower (the second comparison process). As a result, the tendency of the color displayed in is changed between a case where the degree of the change is small in the hue moving image and a case where the degree of the change is large. Thus, the degree of the blood flow variation generated between the first image and the second image can be reflected in the display of the hue moving image in an easy-to-understand manner Further, as illustrated in the third setting process, the information acquisition unit 112 acquires the first pulse wave information indicating the pulse wave of the part of the body based on the image information of the body in the first image obtained by capturing at least the part of the body and acquires the second pulse wave information indicating the pulse wave of the part of the body based on the image information of the body in the second image obtained by capturing the part of the body after the first image has been obtained. The display information determination unit 113 determines the brightness of the display image corresponding to the blood flow variation of the part of the body based on the first pulse wave information and the second pulse wave information (the first comparison process). Alternatively, the brightness of the display image is determined based on the first amplitude indicating the amplitude of the pulse wave acquired from the first pulse wave information and the second amplitude indicating the amplitude of the pulse wave acquired from the second pulse wave information (the second comparison process). Then, the display control unit 115 controls the display of the display image by the display color determined based on the brightness of the display determined by the display information determination unit 113 and the second pulse wave information. As a result, the color changes with a low luminance when the degree of the change in the hue moving image is small, but the color changes brightly with a high luminance when the degree of the change is large. Thus, the degree of the blood flow variation generated between the first image and the second image can be reflected in the display of the hue moving image in an easy-to-understand manner Further, as illustrated in the first to third setting processes, the electronic device 1 performs control to display the hue moving image such that the maximum value of the pulse wave amplitude corresponds to the maximum value of the display range and the minimum value of the pulse wave amplitude corresponds to the minimum value of the display range. As a result, even if the display range changes, the color corresponding to the pulse wave waveform is appropriately set according to the determined display range, and thus, it is possible to appropriately visualize the movement of the blood flow that changes periodically.

As illustrated in the second comparison process, the electronic device 1 includes the information acquisition unit 112, the display information determination unit 113, and the display control unit 115. The display information determination unit 113 determines the display range of the color corresponding to the blood flow variation based on the first amplitude which indicates the amplitude of the pulse wave acquired from the first pulse wave information, and the second amplitude which indicates the amplitude of the pulse wave acquired from the second pulse wave information.

This process also has the same effect as the first comparison process. Since attention is paid to the amplitude, it is possible to more accurately notify the user of the blood flow variation in the two images with different time axes even if the orientation of the user is not appropriate.

[Modifications]

The invention is not limited to the above-described embodiment, and the invention encompasses modifications, improvements, and the like within a scope of achieving the object of the invention. For example, the above-described embodiment may be modified as the following modifications.

Although the description has been made in the above-described embodiment regarding the example in which a display method is selected from among the first display range, the second display range, and the third display range based on the first pulse wave information and the second pulse wave information, the invention is not limited this format. For example, the process of selecting the display range may be omitted, and a process of determining a display range or brightness may be performed in the state of achieving match between a specific value (for example, a median) of a display range of the hue moving image before the treatment generated based on the first pulse wave information and a specific value (for example, a median) of a display range of the hue moving image after the treatment generated based on the second pulse wave information such that the maximum value of the display range (luminance) or brightness of the hue moving image after treatment generated based on the second pulse wave information is larger than the maximum value of the display range (luminance) or brightness of the hue moving image before the treatment generated based on the first pulse wave information. Alternatively, a process of determining a display range or brightness may be performed in the state of achieving match between a specific value (for example, a median) of a display range of the hue moving image before the treatment generated based on the first pulse wave information and a specific value (for example, a median) of a display range of the hue moving image after the treatment generated based on the second pulse wave information such that the minimum value of the display range (luminance) or brightness of the hue moving image after treatment is smaller than the minimum value of the display range (luminance) or brightness of the hue moving image before the treatment.

Alternatively, a process of calculating the maximum value or the minimum value of the display range or brightness according to the degree of the comparison result between the first pulse wave information and the second pulse wave information may be performed. In this process, the larger maximum value of the display range or brightness after the treatment is calculated as the difference between the first pulse wave information and the second pulse wave information decreases. Alternatively, the maximum value of the display range or brightness after the treatment is set to be larger than the maximum value of the display range or brightness before the treatment, and a difference between the maximum value of display range or brightness before the treatment and the maximum value of the display range or brightness after the treatment is set to be larger as compared with the case where the difference between the first pulse wave information and the second pulse wave information is small. In this process, the smaller maximum value of the display range or brightness after the treatment is calculated as the difference between the first pulse wave information and the second pulse wave information decreases. Alternatively, the minimum value of the display range or brightness after the treatment is set to be smaller than the minimum value of the display range or brightness before the treatment, and a difference between the minimum value of display range or brightness before the treatment and the minimum value of the display range or brightness after the treatment is set to be smaller as compared with the case where the difference between the first pulse wave information and the second pulse wave information is large. In this manner, the method for determining the display range and brightness can be changed as appropriate.

Although the hue moving image in which the hue changes are displayed in the mosaic shape has been described as an example in the above-described embodiment, the display format is not limited to this format. For example, a process of displaying the hue moving image at one place (for example, a part of the cheek) may be performed instead of the process of displaying the hue moving image in the mosaic shape. In this case, a process of determining a color to be displayed at a certain time based on the pulse wave information used to determine the display range may be performed.

Although the actual image is combined with the image in the above-described embodiment, but the display format is not limited to this format. It is also possible to adopt a format of creating a hue moving image that matches the avatar image and displaying a blood flow variation in an animation expression that turns pale or red.

It is also possible to adopt a configuration in which the display unit 18 of the electronic device 1 of the above-described embodiment is combined with a mirror unit having a reflection surface. In this case, the mirror unit is implemented using a half mirror having both transmission characteristics and reflection characteristics as optical characteristics. Then, the mirror unit is arranged so as to be superimposed on a front plane of the display unit 18 in a direction visually recognized by the user. With such an arrangement, the user can visually recognize his or her own face reflected by the mirror unit and various kinds of information (for example, a combined image) displayed on the display unit 18 and transmitted through the mirror unit at the same time, for example, instead of the user image captured by the imaging unit 16. That is, the user image captured by the imaging unit 16 as the subject is visually recognized as the actual image of the user in the above-described embodiment, but a mirror image of the user reflected by the mirror unit is visually recognized as the actual image of the user in this modification. Even in this case, the same effects as those of the above-described embodiment can be obtained.

Although the configuration in which the comparison process is performed using the converted luminance value obtained by converting the detected luminance has been described in the above-described embodiment, but the invention is not limited to this configuration. The converted luminance value is one mode indicating a luminance level, and the conversion process may be omitted from the above-described embodiment, and the comparison process may be performed using the detected luminance value without performing the conversion process.

<Other Modifications>

For example, it is assumed that the electronic device 1 and the respective servers included in the server group 3 cooperate with each other in the above-described embodiment. However, the functions of the respective servers may be added to the electronic device 1 such that all the processes are performed only by the electronic device 1.

Further, the electronic device 1 to which the invention is applied has been described by taking an example of the electronic device incorporated in the portable self-standing mirror in the above-described embodiment, but the invention is not particularly limited thereto. For example, the invention can be applied to an electronic device incorporated in a large mirror such as a full-length mirror, an electronic device incorporated in a stationary bathroom vanity, and a mirror-shaped electronic device installed in a bathroom.

The above-described series of processes can be executed by hardware or software. In other words, the functional configuration of FIG. 5 is merely an example and is not particularly limited. That is, it suffices that the electronic device 1 is provided with a function capable of executing the above-described series of processes as a whole, and what kind of functional block is used to realize this function is not particularly limited to the example of FIG. 5.

Further, one functional block may be configured by hardware alone, software alone, or a combination thereof. The functional configuration in the embodiment is implemented by a processor that executes arithmetic processing. The processor that can be used in the embodiment includes not only those configured using various processing devices, such as single processor, a multiprocessor, and a multicore processor, but also a combination of these various processing devices and a processing circuit such as an application specific integrated circuit (ASIC) and a field-programmable gate array (FPGA).

When the series of processes is executed by software, a program that configures the software is installed on a computer or the like from a network or recording medium.

The computer may be a computer embedded in dedicated hardware. Further, the computer may be a computer capable of executing various functions by installing various programs, for example, a general-purpose personal computer.

The recording medium containing such a program is configured using not only the removable medium 100 of FIG. 4, which is distributed separately from the device body to provide the program to the user, but also a recording medium or the like provided to the user in the state of being preliminarily incorporated in the device body. The removable medium 100 is configured using, for example, a magnetic disk (including a floppy disk), an optical disk, a magneto-optical disk, or the like. The optical disc is configured using, for example, a compact disc-read only memory (CD-ROM), a DVD, a Blu-ray (registered trademark) disc (Blu-ray disc), or the like. The magneto-optical disk is configured using a mini-disk (MD) or the like. In addition, the recording medium provided to the user in the state of being preliminarily incorporated in the device body is configured using, for example, the ROM 12 in FIG. 4 in which the program has been recorded, a hard disk included in the storage unit 19 in FIGS. 4 and 5, or the like.

In this specification, the steps describing the program recorded on the recording medium include, of course, not only processes performed in a time-series manner in the order thereof, but also processes which are executed in parallel or individually even if not necessarily processed in a time-series manner. In the present specification, the term "system" means an overall apparatus including a plurality of devices and a plurality of units.

Although some embodiments of the invention have been described as above, these embodiments are merely examples and do not limit the technical scope of the invention. The invention can take various other embodiments, and further, various modifications, such as omission and replacement, can be made within a scope not departing from a gist of the invention. These embodiments and modifications thereof are included in the scope and the gist of the invention described in this specification and the like, and are also included in the inventions described in the claims and a scope of equivalents thereof.

What is claimed is:

1. A control method of an electronic device which measures a blood flow based on an image of a body and includes at least one processor, the control method being performed by the processor, and the method comprising:
 acquiring first pulse wave information indicating a pulse wave of a part of a body based on image information of the body in a first image obtained by imaging at least the part of the body;

acquiring second pulse wave information indicating a pulse wave of the part of the body based on image information of the body in a second image obtained by imaging the part of the body after the first image has been obtained;

determining a display range of a display color of a display image to be displayed, the display image displaying, in hue, a state of a blood flow corresponding to a blood flow variation of the pulse wave indicated by the first pulse wave information and the pulse wave indicated by the second pulse wave information, and the display range of the display color being determined based on a difference between the first pulse wave information and the second pulse wave information;

controlling display of the display image to be displayed with the display color determined based on the display range and the second pulse wave information;

setting a range width of the display range centered on a color corresponding to a center coordinate of the display range to be wider than a range width of the display range applied when the difference between the first pulse wave information and the second pulse wave information is relatively low as the difference between the first pulse wave information and the second pulse wave information increases; and setting the range width of the display range centered on the color corresponding to the center coordinate of the display range to be narrower than a range width of the display range applied when the difference between the first pulse wave information and the second pulse wave information is relatively high as the difference between the first pulse wave information and the second pulse wave information decreases.

2. The method according to claim 1, wherein the blood flow variation is a variation from a blood flow of the part of the body in the first image to the blood flow of the part of the body in the second image.

3. The method according to claim 1, wherein the display of the display image is controlled based on the second pulse wave information including information which is a difference between a peak and a bottom of luminances corresponding to the pulse wave of the part of the body when capturing the second image.

4. The method according to claim 1, wherein a moving image is displayed as the display image.

5. The method according to claim 1, wherein:
the first pulse wave information is acquired based on first luminance information included in the image information of the body in the first image; and
the second pulse wave information is acquired based on second luminance information included in the image information of the body in the second image.

6. The method according to claim 5, wherein:
the first luminance information is information on a luminance value of at least one pixel in the part of the body in the first image or an average luminance of an entire region corresponding to the part of the body in the first image, and
the second luminance information is information on a luminance value of one pixel in the part of the body in the second image or an average luminance of an entire region corresponding to the part of the body in the second image.

7. The method according to claim 1, wherein:
the first image and the second image are moving images, and the display range of the display color is determined based on a difference between a first baseline acquired based on the first pulse wave information and a second baseline acquired based on the second pulse wave information.

8. The method according to claim 7, wherein:
the first baseline is acquired based on an average value of luminance values corresponding to a pulse wave in a range where the pulse wave is stable in the first pulse wave information, and
the second baseline is acquired based on an average value of luminance values corresponding to a pulse wave of a range where the pulse wave is stable in the second pulse wave information.

9. A control method of an electronic device which measures a blood flow based on an image of a body and includes at least one processor, the control method being performed by the processor, and the method comprising:

acquiring first pulse wave information indicating a pulse wave of a part of a body based on image information of the body in a first image obtained by imaging at least the part of the body;

acquiring second pulse wave information indicating a pulse wave of the part of the body based on image information of the body in a second image obtained by imaging the part of the body after the first image has been obtained;

determining a display range of a display color of a display image to be displayed, the display image displaying, in hue, a state of a blood flow corresponding to a blood flow variation of the pulse wave indicated by the first pulse wave information and the pulse wave indicated by the second pulse wave information, and the display range of the display color being determined based on a difference between the first pulse wave information and the second pulse wave information;

controlling display of the display image to be displayed with the display color determined based on the display range and the second pulse wave information;

setting, as the display range, a range on a higher coordinate side of a range of the display range applied when the difference between the first pulse wave information and the second pulse wave information is relatively low among ranges of the display range as the difference between the first pulse wave information and the second pulse wave information increases; and setting, as the display range, a range on a lower coordinate side of a range of the display range applied when the difference between the first pulse wave information and the second pulse wave information is relatively high among the ranges of the display range as the difference between the first pulse wave information and the second pulse wave information decreases.

10. The method according to claim 9, wherein the blood flow variation is a variation from a blood flow of the part of the body in the first image to the blood flow of the part of the body in the second image.

11. The method according to claim 9, wherein the display of the display image is controlled based on the second pulse wave information including information which is a difference between a peak and a bottom of luminances corresponding to the pulse wave of the part of the body when capturing the second image.

12. The method according to claim 9, wherein a moving image is displayed as the display image.

13. The method according to claim 9, wherein:
the first pulse wave information is acquired based on first luminance information included in the image information of the body in the first image; and
the second pulse wave information is acquired based on second luminance information included in the image information of the body in the second image.

14. The method according to claim 13, wherein:
the first luminance information is information on a luminance value of at least one pixel in the part of the body in the first image or an average luminance of an entire region corresponding to the part of the body in the first image, and
the second luminance information is information on a luminance value of one pixel in the part of the body in the second image or an average luminance of an entire region corresponding to the part of the body in the second image.

15. The method according to claim 9, wherein:
the first image and the second image are moving images, and
the display range of the display color is determined based on a difference between a first baseline acquired based on the first pulse wave information and a second baseline acquired based on the second pulse wave information.

16. The method according to claim 15, wherein:
the first baseline is acquired based on an average value of luminance values corresponding to a pulse wave in a range where the pulse wave is stable in the first pulse wave information, and
the second baseline is acquired based on an average value of luminance values corresponding to a pulse wave of a range where the pulse wave is stable in the second pulse wave information.

17. A control method of an electronic device which measures a blood flow based on an image of a body and includes at least one processor, the control method being performed by the processor, and the method comprising:
acquiring first pulse wave information indicating a pulse wave of a part of a body based on image information of the body in a first image obtained by imaging at least the part of the body;
acquiring second pulse wave information indicating a pulse wave of the part of the body based on image information of the body in a second image obtained by imaging the part of the body after the first image has been obtained;
determining a display range of a display color of a display image to be displayed, the display image displaying, in hue, a state of a blood flow corresponding to a blood flow variation of the pulse wave indicated by the first pulse wave information and the pulse wave indicated by the second pulse wave information, and the display range of the display color being determined based on a first amplitude indicating an amplitude of a pulse wave acquired from the first pulse wave information and a second amplitude indicating an amplitude of a pulse wave acquired from the second pulse wave information;
controlling display of the display image to be displayed with the display color determined based on the display range and the second pulse wave information; and
setting a range width of the display range centered on a color corresponding to a center coordinate of the display range based on an increase rate of the second amplitude relative to the first amplitude.

18. The method according to claim 17, wherein the setting comprises:
setting the range width of the display range centered on the color corresponding to the center coordinate of the display range to be wider than a range width of the display range applied when the increase rate of the second amplitude relative to the first amplitude is relatively low as the increase rate of the second amplitude relative to the first amplitude is higher; and
setting the range width of the display range centered on the color corresponding to the center coordinate of the display range to be narrower than a range width of the display range applied when the increase rate of the second amplitude relative to the first amplitude is relatively high as the increase rate of the second amplitude relative to the first amplitude is lower.

19. The method according to claim 17, wherein the setting comprises:
setting, as the display range, a range on a higher coordinate side of a range of the display range applied when the increase rate of the second amplitude relative to the first amplitude is relatively low among ranges of the display range as the increase rate of the second amplitude relative to the first amplitude is higher; and
setting, as the display range, a range on a lower coordinate side of a range of the display range of the display color applied when the increase rate of the second amplitude relative to the first amplitude is relatively high among the ranges of the display range as the increase rate of the second amplitude relative to the first amplitude is lower.

* * * * *